United States Patent [19]

Beck et al.

[11] Patent Number: 5,032,606

[45] Date of Patent: Jul. 16, 1991

[54] NOVEL FLUORINATED RESORCINOL ETHERS AND THEIR USE AS ANTI-ALLERGICS AND ANTI-INFLAMMATORIES

[75] Inventors: Andreas Beck, Freiburg, Fed. Rep. of Germany; Alfred Sallmann, Bottmingen, Switzerland; Robert W. Lang, Pratteln, Switzerland; Paul Wenk, Allschwil, Switzerland

[73] Assignee: Ciba-Geigy Corporation, Ardsley, N.Y.

[21] Appl. No.: 529,690

[22] Filed: May 23, 1990

Related U.S. Application Data

[60] Continuation of Ser. No. 297,724, Jan. 17, 1989, abandoned, which is a division of Ser. No. 3,156, Jan. 14, 1987, Pat. No. 4,820,726, which is a continuation-in-part of Ser. No. 801,012, Nov. 22, 1985, abandoned.

[30] Foreign Application Priority Data

Sep. 17, 1985 [CH] Switzerland .................. 4016/85

[51] Int. Cl.⁵ .................. C07D 257/06; A61K 31/41
[52] U.S. Cl. .................. 514/381; 548/251; 548/252; 548/253
[58] Field of Search .................. 514/381; 548/251, 252, 548/253

[56] References Cited

U.S. PATENT DOCUMENTS

| | | | |
|---|---|---|---|
| 3,329,694 | 7/1967 | Martel .................. | 260/410.9 |
| 3,467,715 | 9/1969 | Breeadbent .................. | 260/592 |
| 3,966,965 | 6/1976 | Sellatedt .................. | 424/309 |
| 4,119,783 | 10/1978 | Hall et al. .................. | 560/43 |
| 4,159,278 | 6/1979 | Hall et al. .................. | 260/501.15 |
| 4,442,115 | 4/1984 | Ramuden et al. .................. | 424/269 |
| 4,448,729 | 5/1984 | Klaubert .................. | 260/465 |
| 4,483,707 | 11/1984 | Breitenstein .................. | 79/94 |
| 4,507,498 | 3/1985 | Carson et al. .................. | 562/463 |
| 4,672,073 | 6/1987 | Nohara et al. .................. | 548/253 |
| 4,808,604 | 2/1989 | Beck et al. .................. | 514/381 |
| 4,863,942 | 9/1989 | Wenk et al. .................. | 514/381 |

FOREIGN PATENT DOCUMENTS

| | | |
|---|---|---|
| 28063 | 5/1981 | European Pat. Off. . |
| 123541 | 10/1984 | European Pat. Off. . |
| 132366 | 1/1985 | European Pat. Off. . |
| 132367 | 1/1985 | European Pat. Off. . |
| 147973 | 7/1985 | European Pat. Off. . |
| 2151227 | 7/1985 | United Kingdom .................. 548/253 |

OTHER PUBLICATIONS

Chem. Abstract, 88, 37429q (1978).
Chem. Abstract, 93, 26100c (1980).
Chem. Abstract 89, 129265g (1978).

*Primary Examiner*—David B. Springer
*Attorney, Agent, or Firm*—JoAnn Villamizar

[57] ABSTRACT

4-Acylresorcinol ethers of the formula

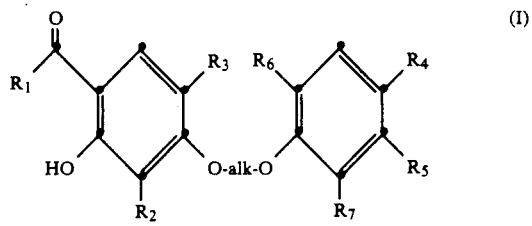

in which $R_1$ is lower alkyl, $R_2$ is fluorinated lower alkyl, $R_3$ is hydrogen, lower alkoxy, trifluoromethyl or halogen, alk is an alkylene or hydroxyalkylene radical which is uninterrupted or interrupted by oxygen, one of the radicals $R_4$, $R_5$ and $R_7$ is a group of the formula $-NH-C(=O)-R_8$, a radical $R_4$ or $R_5$ which differs from this is a radical $R_9$ and a radical $R_7$ which differs from this is a radical $R_{10}$, $R_6$ is hydrogen, lower alkyl, trifluoromethyl, halogen, carboxyl which is free, esterified or amidated, cyano or lower alkanoyl, $R_8$ is carboxyl which is free, esterified or amidated or 5-tetrazolyl, $R_9$ is hydrogen, lower alkyl, lower alkoxy, halogen or trifluoromethyl and $R_{10}$ is hydrogen, lower alkyl, lower alkoxy, halogen, trifluoromethyl, cyano or carboxyl which is free, esterified or amidated, and their salts have antiallergic and antiinflammatory properties.

12 Claims, No Drawings

NOVEL FLUORINATED RESORCINOL ETHERS AND THEIR USE AS ANTI-ALLERGICS AND ANTI-INFLAMMATORIES

This is a continuation of Ser. No. 297,724 filed Jan. 17, 1989, abandoned, which is a division of application Ser. No. 003,156 filed on Jan. 14, 1987, U.S. Pat. No. 4,820,726, which is a continuation-in-part application of our co-pending application Ser. No. 801,012 filed Nov. 22, 1985, abandoned.

The invention relates to novel 2-fluoroalkylated 4-acylresorcinol ethers of the formula

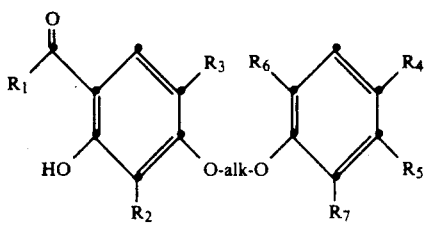
(I)

in which $R_1$ is lower alkyl, $R_2$ is fluorinated lower alkyl, $R_3$ is hydrogen, lower alkoxy, trifluoromethyl or halogen, alk is an alkylene or hydroxyalkylene radical which is uninterrupted or interrupted by oxygen, one of the radicals $R_4$, $R_5$ and $R_7$ is a group of the formula —NH—C(=O)—$R_8$, a radical $R_4$ or $R_5$ which differs from this is a radical $R_9$ and a radical $R_7$ which differs from this is a radical $R_{10}$, $R_6$ is hydrogen, lower alkyl, trifluoromethyl, halogen, carboxyl which is free, esterified or amidated, cyano or lower alkanoyl, $R_8$ is carboxyl which is free, esterified or amidated or 5-tetrazolyl, $R_9$ is hydrogen, lower alkyl, lower alkoxy, halogen or trifluoromethyl and $R_{10}$ is hydrogen, lower alkyl, lower alkoxy, halogen, trifluoromethyl, cyano or carboxyl which is free, esterified or amidated, and salts thereof.

Alkylene radicals alk can have not more than 9 chain members and are, for example, straight-chain alkylene radicals of the formula $$-(CH_2)_m-$$ (Ia)

in which m is an integer from 2 to not more than 9, but can also be alkylene radicals which are branched, in particular in positions which are higher than the α-position and lower than the ω-position, and are preferably lower alkylene radicals (straight-chain and branched) of the type mentioned.

Alkylene radicals interrupted by oxygen are, for example, mono-, di- or trioxaalkylene radicals, for example of the formula $$-(CH_2)_{n'}-O-(CH_2)_n]_k$$ (Ib)

in which n and n' independently of one another are 2, 3 or 4 and k is 1, 2 or 3, and are, in particular, oxa- or dioxa-lower alkylene radicals, for example of the formula Ib in which n and n' is 2 and k is 1 or 2.

Hydroxyalkylene radicals which are uninterrupted or interrupted by oxygen are, for example, hydroxyalkylene, hydroxy(oxa)alkylene or hydroxy(dioxa)alkylene radicals in which the hydroxyl group is bonded in a position higher than the α-position and lower than the ω-position, for example radicals of the formula $$-(CH_2)_{l'}-O]_oCH_2CH(OH)CH_2-O-(CH_2)_l]_p$$ (Ic)

in which l and l' independently of one another are 2 or 3 and o and p independently of one another are 0 or 1, and are, in particular, corresponding hydroxy-lower alkylene radicals, and furthermore hydroxy(oxa)-lower alkyl radicals.

Esterified carboxyl is, for example, lower alkoxycarbonyl, but in the case of $R_8$, can also be N,N-di-lower alkylamino-lower alkoxycarbonyl, N,N-lower alkyleneamino-lower alkoxycarbonyl, substituted or unsubstituted N,N-(aza)-lower alkyleneamino-lower alkoxycarbonyl, N,N-(oxa)-lower alkyleneamino-lower alkoxycarbonyl or N,N-(thia)-lower alkyleneamino-lower alkoxycarbonyl.

Amidated carboxyl is, for example, carbamyl, N-mono- or N,N-di-lower alkylcarbamyl, and furthermore N,N-lower alkylene-, N,N-(aza)-lower alkylene-, N,N-(oxa)-lower alkylene- or N,N-(thia)-lower alkylene-carbamyl.

"Lower" organic compounds above and below and groups derived therefrom are to be understood, for example, as those which contain not more than 7, in particular not more than 4, carbon atoms (C atoms).

Fluorinated lower alkyl has, for example, not more than 3, in particular terminally bonded, fluorine atoms and is, for example, mono-, di- or trifluoro-$C_1$-$C_4$-alkyl, such as trifluoromethyl, 3-fluoropropyl, 3,3-difluoropropyl or 3,3,3-trifluoropropyl.

Lower alkyl is, for example, $C_1$-$C_4$-alkyl, such as methyl, ethyl, propyl, isopropyl or butyl, and furthermore secondary or tertiary butyl.

Lower alkoxy is, for example, $C_1$-$C_4$-alkoxy, such as methoxy, ethoxy, propoxy, isopropoxy or butoxy.

Halogen has, for example, an atomic number of not more than 53, in particular 17 to not more than 53, and is, for example, fluorine, chlorine, bromine or iodine.

Lower alkanoyl is, for example, $C_1$-$C_7$-alkanoyloxy, such as formyl, acetyl, propionyl, butyryl, valeroyl or pivaloyl.

Straight-chain lower alkylene is, for example, straight-chain $C_2$-$C_7$-alkylene, such as ethylene, 1,3-propylene, 1,4-butylene, 1,5-pentylene, 1,6-hexylene or 1,7-heptylene, but can also be 1,2-propylene, 1,3-butylene or 2,4-pentylene.

Branched lower alkylene is, for example, branched $C_4$-$C_6$-alkylene, such as 1,3-(2-methyl)-propylene or 1,3-(2,2-dimethyl)propylene.

Oxa-lower alkylene is, for example, 3- or 4-oxa-$C_5$-$C_7$-alkylene, such as 1,5-(3-oxa)pentylene or 1,7-(4-oxa)heptylene; dioxa-lower alkylene is, for example, 1,7-(3,5-dioxa)heptylene.

Hydroxy-lower alkylene is, for example, 2-, 3- or 4-hydroxy-$C_3$-$C_7$-alkylene, such as 1,3-(2-hydroxy)propylene, 1,4-2-hydroxy)butylene, 1,5-(3-hydroxy)pentylene, 1,6-(2-hydroxy)hexylene or 1,7-(4-hydroxy)heptylene. Hydroxy(oxa)-lower alkylene is, for example, 2-hydroxy-4-oxa-$C_6$-$C_7$-alkylene, such as 1,6-(2-hydroxy-4-oxa)hexylene or 1,7-(2-hydroxy-4-oxa)heptylene.

Lower alkoxycarbonyl is, for example, $C_1$-$C_4$-alkoxycarbonyl, such as methoxy-, ethoxy-, propoxy-, isopropoxy- or butoxycarbonyl.

N,N-Di-lower alkylamino-lower alkoxycarbonyl is, for example, N,N-di-$C_1$-$C_4$-alkylamino-$C_2$-$C_4$-alkoxycarbonyl, such as 2-(dimethylamino)ethoxycarbonyl, 2-(diethylamino)ethoxycarbonyl or 3-(dimethylamino)propoxycarbonyl.

N,N-Lower alkyleneamino-lower alkoxycarbonyl is, for example, 5-membered to 7-membered N,N-alkyleneamino-$C_2$-$C_4$-alkoxycarbonyl, such as 2-(pyrrolidino)-, 2-(piperidino)- or 2-(tetrahydroazepino)ethoxycarbonyl.

Substituted or unsubstituted N,N-(aza)-lower alkyleneamino-lower alkoxycarbonyl is, for example, 5-membered to 7-membered N,N-(aza)alkyleneamino-$C_2$-$C_4$-alkoxycarbonyl, such as 2-(piperazino)ethoxycarbonyl or 2-(4-methylpiperazino)ethoxycarbonyl.

N,N-(Oxa)- or N,N-(thia)-lower alkylamino-lower alkoxycarbonyl is, for example, 5-membered to 7-membered N,N-(oxa)-or N,N-(thia)-alkyleneamino-$C_2$-$C_4$-alkoxycarbonyl, such as 2-(morpholino)- or 2-(thiomorpholino)ethoxycarbonyl.

N-Mono- or N,N-di-lower alkylcarbamyl is, for example, N-$C_1$-$C_7$-alkyl- or N,N-di-$C_1$-$C_4$-alkylcarbamyl, such as N-methyl-, N-ethyl- or N,N-dimethylcarbamyl.

N,N-Lower alkylenecarbamyl or N,N-(aza)-, N,N-(oxa)- or N,N-(thia)-lower alkylenecarbamyl is, for example, 5-membered to 7-membered N,N-alkylene-, N,N-(aza)alkylene-, N,N-(oxa)alkylene- or N,N-(thia)alkylenecarbamyl, such as pyrrolidino-, piperidino-, pyridazino-, (4-methyl)piperazino-, morpholino- or thiomorpholinocarbonyl.

Preferred salts of compounds of the formula I are pharmaceutically acceptable salts, such as metal salts, ammonium salts or salts with organic bases. Metal salts are, for example, corresponding alkali metal and alkaline earth metal salts, for example lithium, sodium, potassium, magnesium or calcium salts, and furthermore pharmaceutically acceptable transition metal salts, such as zinc or copper salts. Salts with organic bases are formed, for example, from compounds of the formula I in which $R_6$ and/or $R_7$ is carboxyl and/or $R_8$ is carboxyl or 5-tetrazolyl with mono-, di- or trisubstituted organic amines, such as corresponding alkylamines, hydroxyalkylamines, suitable heterocyclic compounds containing at least one N atom, such as morpholine, thiomorpholine, piperidine or pyrrolidine, amino-saccharides which may or may not be N-substituted, for example with N-methyl-D-glucamine, or basic amino acids, such as lysine, arginine, histidine or ornithine, those with the L-configuration being preferred. Alkylamines are, for example, mono-, di- or tri-lower alkylamines, such as ethyl-, tert.-butyl-, diethyl-, diisopropyl-, trimethyl- or triethylamine. Hydroxyalkylamines are, for example, mono-, di- or trihydroxyalkylamines, such as mono-, di- or triethanolamine or diisopropanolamine, or hydroxy-lower alkyl-lower alkylamines, such as N,N-dimethyl- or N,N-diethylamino-ethanol or tri(hydroxymethyl)methylamine.

Other salts are pharmaceutically acceptable acid addition salts, such as hydrohalides, methanesulfonates, N-cyclohexylsulfamates, maleinates, fumarates, maleates or tartrates of compounds of the formula I in which the radical $R_8$ is capable of forming corresponding salts.

The compounds of the formula I with chiral C atoms can, depending on the number thereof, be present in forms which are enantiomeric or diastereomeric with respect to one another or as mixtures thereof, such as diastereomer mixtures, racemates or racemate mixtures.

The novel compounds are distinguished by useful pharmacological properties.

Thus, they have an antiallergic action based on a pronounced $LTD_4$-(leucotriene-$D_4$)- and PAF-(PAF-acetoether)-antagonism. The $LTD_4$-antagonistic properties of the compounds according to the invention can be demonstrated, for example, in vitro by means of their inhibiting effect, detectable in concentrations from about 0.03 to about 0.10 μmol/l, on contractions triggered off on the isolated guinea-pig ileum by $LTD_4$, and in vivo by means of their inhibiting effect, detectable on intravenous treatment in doses from about 0.08 mg/kg or on aerosol treatment from an active ingredient content of about 0.025% by weight, on bronchospasms in guinea-pigs triggered off by $LTD_4$. They furthermore have a pronounced inhibition on $LTD_4$ synthesis, which can be demonstrated in vitro by means of the inhibition of aggregation of peritoneal PMN in rats.

In comparison with antiallergic compounds of similar structure, the compounds according to the invention are distinguished by a longer duration of action and, in addition to the above $LTD_4$-antagonistic action, exhibit phospholipase-inhibiting properties which are novel for this class of compound and a pronounced anti-inflammatory and dermatophlogistatic action as well as a pronounced inhibiting effect on leucotriene-$B_4$ biosynthesis, such as can be demonstrated in vitro in concentrations from about 0.5 μmol/l, these properties already themselves being very useful and also supplementing the antiallergic action in a desirable manner. The phospholipase-inhibiting properties can be demonstrated, for example, in vitro by means of the inhibition, detectable in concentrations from about 10 μmol/l, of the activity of phospholipases $A_2$ (from human leucocytes) and C (from human platelets), and the antiinflammatory or dermatophlogistic properties can be demonstrated in vivo by means of the inhibiting effect, in concentrations from about 10 mg/ml, on experimental croton oil ear oedema in rats.

The compounds according to the invention can accordingly be used as antiallergics, for example for the treatment of asthma, hayfever, rhinitis and skin allergies, but in particular as antiinflammatories, especially for the treatment of inflammatory rheumatic diseases, and as skin and mucous membrane phlogistatics, for the treatment of inflammatory dermatoses of the most diverse origins, but especially of allergic origin, for example for the treatment of inflammatory skin irritations, contact dermatitis, exanthema, burns and inflammations of the mucosa of the eyes, lips, mouth and genital or anal region.

The inhibiting effect on experimental ear oedema in rats can be achieved in accordance with the method of G. Tonelli and L. Thibault, Endocrinology 77, 625 (1965). The following experimental designs, for example, can be used to determine the other properties mentioned.

Inhibiting effect on $LTD_4$-Induced Contractions of the Guinea-Pig Ileum

Contractions are triggered off by synthetic $LTD_4$ (leucotriene $D_4$, potassium salt) on ileum segments which have been taken from guinea-pigs with a body weight of 300 to 400 g, fixed in an organ bath in Tyrode solution (38° C., gassing with 95% of $O_2$ and 5% of $CO_2$) and loaded with 1p, and the degree of the contractions is recorded. The degree of inhibition of these contractions to be attributed to the $LTD_4$-antagonistic action of the test substance is measured. The concentration, designated the $IC_{50}$, of the test substance which reduces $LTD_4$-induced contractions to 50% of the starting value is determined. In this experimental design, for example, an $IC_{50}$ value of 0.087 μmol/l was obtained for the sodium salt of N-{3-[3-(4-acetyl-3-hydroxy-2-propyl-phenoxy)-2-hydroxypropoxy]-2-cyano-phenyl}-oxamic acid according to U.S. Pat. No. 4,448,729 and an $IC_{50}$ value of 0.01 μmol/l was obtained for the sodium salt of N-{{3-{3-[4-acetyl-3-hydroxy-2-(3,3,3-trifluoropropyl)-phenoxy]-propoxy}-4-bromo-6-methyl-pheny}}-1H-tetrazole-5-carboxamide according to the application.

In Vitro Test for the Determination of the Inhibition of Phospholipase $A_2$ from Human Leucocytes Neutrophilic polymorphonuclear human leucocytes are isolated, starting from "buffy coats" by multi-stage fractional sedimentation and are deep-frozen. The phospholipase $A_2$ is extracted from the cell suspension by homogenisation with the addition of ice-cold 0.36N $H_2SO_4$ in 2M NaCl, and the supernatant obtained after centrifugation at 10,000 g is dialysed against sodium acetate buffer, pH 4.5.

To determine the enzyme activity, the enzyme (10-30 μg of protein) is incubated in 0.1M tris/HCl buffer, pH 7, with the addition of 1 mM $CaCl_2$ and substrate consisting of phospholipids (2 μM), radioactively labelled biosynthetically with $^{14}C$-oleic acid, of *Escherichia coli*, at 37° C. for 1 hour. The reaction is stopped by addition of Dole reagent (isopropanol/heptane/1N $H_2SO_4$ 40:10:1, volume/volume) and the $^{14}C$-oleic acid released selectively by phospholipase $A_2$ is extracted. The substrate also co-extracted is removed completely by filtration of the extract through a silica gel column. The $^{14}C$-oleic acid in the eluate is determined by radiometry.

To determine an inhibiting effect of test substances on the phospholipase $A_2$, these are added to the incubation batch as solutions in water, dimethylsulfoxide (final concentration in the batch up to 5 vol %) or ethanol (final concentration in the batch up to 2.5 vol %). The action potency of the test substances is expressed by the $IC_{50}$, i.e. the concentration which causes an inhibition of 50% of the control activity. The $IC_{50}$ is determined graphically by plotting the percentage inhibition on the ordinate against the logarithm of the concentration (μM) on the abscissa.

In this experimental design, for example, an $IC_{50}$ value of 12 μmol/l was obtained for the sodium salt of N-{{3-{3-[4-acetyl-3-hydroxy-2-(3,3,3-trifluoropropyl)-phenoxy]-propoxy}-4-bromo-6-methyl-phenyl}}-1H-tetrazole-5-carboxamide and an $IC_{50}$ value of 13 μmol/l was obtained for N-{{3-{3-[4-acetyl-3-hydroxy-2-(3,3,3-trifluoropropyl)-phenoxy]-propoxy}-4-chloro-6-methyl-phenyl}}-1H-tetrazole-5-carboxamide, whilst the sodium salt of N-{3-[3-(4-acetyl-3-hydroxy-2-propyl-phenoxy)-2-hydroxy-propoxy]-2-cyano-phenyl}-oxamic acid according to U.S. Pat. No. 4,448,729 still showed no action even at 100 μmol/l.

Calcium ionophore-induced synthesis of $LTB_4$

Peritoneal exudate (neutrophiles) of Wistar rats (RA 25, male) are obtained 24 hours after intraperitoneal injection of 12% sodium caseinate. Cells ($1 \times 10^7$/ml) are stimulated by Ca ionophore A 23187 ($1 \times 10^{-6}$M) for 4 minutes. Supernatants are investigated for their ability to trigger off PMN aggregation in vitro. Inhibiting substances in dimethylsulfoxide are added 5 minutes before the addition of the ionophore.

The results are given in % inhibition of the control (without an inhibitor) and as the $IC_{50}$.

The invention particularly relates to compounds of the formula I in which $R_1$ is lower alkyl, $R_2$ is fluorinated lower alkyl having not more than 3 fluorine atoms, $R_3$ is hydrogen, lower alkoxy, trifluoromethyl or halogen, alk is lower alkylene or hydroxy-lower alkylene which is uninterrupted or interrupted by oxygen, in particular a radical of the formula $-(CH_2)_m-$ (Ia), $-(CH_2)_{n'}-[O-(CH_2)_n]_{-k}$ (Ib) or $-(CH_2)_{l'}-O]_oCH_2-CH(OH)-CH_2-O-(CH_2)_l]_p$ (Ic), in which k is 1, 2 or 3, and l' independently of one another are 2 or 3, m is an integer from 2 to not more than 9, n and n' independently of one another are 2, 3 or 4 and o and p independently of one another are 0 or 1, one of the radicals $R_4$, $R_5$ and $R_7$ is a group of the formula $-NH-C(=O)-R_8$, a radical $R_4$ or $R_5$ which differs from this is a radical $R_9$ and a radical $R_7$ which differs from this is a radical $R_{10}$, $R_6$ is hydrogen, lower alkyl, trifluoromethyl, halogen, lower alkanoyl, carboxyl, lower alkoxycarbonyl, cyano, carbamyl or N-mono- or N,N-di-lower alkylcarbamyl, $R_8$ is on the one hand carboxyl, lower alkoxycarbonyl, N,N-di-lower alkylamino-lower alkoxycarbonyl, N,N-lower alkyleneamino-lower alkoxycarbonyl, carbamyl, N-mono- or N,N-di-lower alkyl-carbamyl or N,N-lower alkylene- or N,N-(aza)-lower alkylene-, N,N-(oxa)-lower alkylene- or N,N-(thia)-lower alkylene-carbamyl, or on the other hand 5-tetrazolyl, $R_9$ is hydrogen, lower alkyl, lower alkoxy, halogen or trifluoromethyl and $R_{10}$ is hydrogen, lower alkyl, lower alkoxy, halogen, trifluoromethyl, carboxyl, lower alkoxycarbonyl, cyano, carbamyl or N-mono- or N,N-di-lower alkylcarbamyl, and their salts, in particular pharmaceutically acceptable salts.

The invention preferably relates to compounds of the formula I in which $R_1$ is lower alkyl having not more than 4 C atoms, such as methyl, $R_2$ is ω-fluoro-, ω,ω-difluoro- or ω,ω,ω-trifluoro-lower alkyl having not more than 4 C atoms, such as trifluoromethyl or 3,3,3-trifluoropropyl, or furthermore 3-fluoropropyl or 3,3-difluoropropyl, $R_3$ is hydrogen, $R_4$ is hydrogen, lower alkyl, such as methyl, trifluoromethyl or halogen with an atomic number of not more than 35, such as chlorine or bromine, $R_5$ is oxaloamino, lower alkoxyoxalylamino with 3 to not more than 6 C atoms, such as methoxy- or ethoxyoxalylamino, or 5-tetrazolylcarbonylamino, $R_6$ is hydrogen, lower alkyl having not more than 4 C atoms, such as methyl, halogen with an atomic number of not more than 35, such as chlorine or bromine, trifluoromethyl, lower alkoxycarbonyl having not more than 5 C atoms, such as ethoxycarbonyl, cyano or carbamyl, $R_7$ is hydrogen, lower alkyl having not more than 4 C atoms, such as methyl, halogen with an atomic number of not more than 35, such as chlorine, carbamyl or cyano and alk is straight-chain, terminally bonded lower alkylene having 2 to not more than 5 C atoms, such as 1,3-propylene, or hydroxy-lower alkylene having 3 to not more than 7 C atoms, in which the hydroxyl group is bonded in a position higher than the α-position and lower than the ω-position, such as 1,3-(2-hydroxy)-propylene, and their salts, in particular pharmaceutically acceptable salts, with bases.

The invention particularly relates to compounds of the formula I in which $R_1$ is lower alkyl having not more than 4 C atoms, such as methyl, $R_2$ is ω-fluoro-, ω,ω-difluoro- or ω,ω,ω-trifluoro-lower alkyl having not more than 4 C atoms, such as 3,3,3-trifluoropropyl, or furthermore 3-fluoropropyl or 3,3-difluoropropyl, $R_3$ is hydrogen, $R_4$ is hydrogen, lower alkyl, such as methyl, trifluoromethyl or halogen with an atomic number of not more than 35, such as chlorine or bromine, $R_5$ is oxaloamino, 5-tetrazolylcarbonylamino, or, less preferably, lower alkoxyoxalylamino having 3 to not more than 6 C atoms, such as methoxy- or ethoxyoxalylamino, $R_6$ is hydrogen, lower alkyl having not more than 4 C atoms, such as methyl, halogen with an atomic number of not more than 35, such as chlorine or bromine, trifluoromethyl or cyano, $R_7$ is hydrogen, lower alkyl having not more than 4 C atoms, such as methyl, cyano or halogen with an atomic number of not more than 35, such as chlorine or bromine, and alk is straight-chain, terminally bonded lower alkylene having 2 to not more than 5 C atoms, such as 1,3-propylene, or hydroxy-lower alkylene having 3 to not more than 7 C atoms, in which the hydroxyl group is bonded in a position higher than the α-position and lower than the ω-position, such as 1,3-(2-hydroxy)propylene, and their salts, in particular pharmaceutically acceptable salts, with bases.

The invention relates very particularly to compounds of the formula I in which $R_1$ is lower alkyl having not more than 4 C atoms, such as methyl, $R_2$ is ω,ω,ω-trifluoro-lower alkyl having not more than 3 C atoms, such as 3,3,3-trifluoropropyl, $R_3$ is hydrogen and $R_5$ is oxaloamino or 5-tetrazolylcarbonylamino, $R_4$ is lower alkyl having not more than 4 C atoms, such as methyl, $R_6$ is halogen with an atomic number of not more than 35, such as chlorine or bromine, or cyano and $R_7$ is hydrogen and alk is straight-chain, terminally bonded lower alkylene having 2 to not more than 5 C atoms, such as 1,3-propylene, or furthermore hydroxy-lower alkylene having 3 to not more than 7 C atoms, in which the hydroxyl group is bonded in a position higher than the α-position and lower than the ω-position, such as 1,3-(2-hydroxy)propylene, and their salts, in particular pharmaceutically acceptable salts, with bases.

The invention predominantly relates to compounds of the formula I in which $R_1$ is lower alkyl having not more than 4 C atoms, such as methyl, $R_2$ is ω-fluoro-,ω,ω-difluoro- or ω,ω,ω-trifluoro-lower alkyl having not more than 3 C atoms, such as 3,3,3-trifluoropropyl, $R_3$ and $R_7$ are hydrogen, $R_4$ is hydrogen or lower alkyl having not more than 4 C atoms, such as methyl, $R_6$ is hydrogen, cyano or halogen with an atomic number of not more than 35, such as fluorine, chlorine or bromine, $R_5$ is oxaloamino or 5-tetrazolylcarbonylamino and alk is straight-chain, terminally bonded lower alkylene having 2 to not more than 5 C atoms, such as 1,3-propylene, or furthermore hydroxy-lower alkylene having 3 to not more than 7 C atoms, in which the hydroxyl group is bonded in a position higher than the α-position and lower than the ω-position, such as 1,3-(2-hydroxy)propylene, and their salts, in particular pharmaceutically acceptable salts, with bases.

The invention above all relates to compounds of the formula I in which $R_1$ is lower alkyl having not more than 4 C atoms, such as methyl, $R_2$ is ω-fluoro-,ω,ω-difluoro- or ω,ω,ω-trifluoro-lower alkyl having not more than 3 C atoms, such as 3,3,3-trifluoropropyl, $R_3$ and $R_7$ are hydrogen, one of the radicals $R_4$ and $R_6$ is lower alkyl having not more than 4 C atoms, such as methyl, and the other is halogen with an atomic number of not more than 35, such as fluorine, chlorine or bromine, $R_5$ is oxaloamino or 5-tetrazolylcarbonylamino and alk is straight-chain, terminally bonded lower alkylene having 2 to not more than 5 C atoms, such as 1,3-propylene, or furthermore hydroxy-lower alkylene having 3 to not more than 7 C atoms, in which the hydroxyl group is bonded in a position higher than the α-position and lower than the ω-position, such as 1,3-(2-hydroxy)propylene, and their salts, in particular pharmaceutically acceptable salts, with bases.

In particular, the invention relates to the compounds of the formula I mentioned in the examples and their salts, in particular pharmaceutically acceptable salts, with bases.

The invention furthermore relates to a process, based on methods which are known per se, for the preparation of compounds of the formula I and their salts. This comprises a) rearranging a compound of the formula

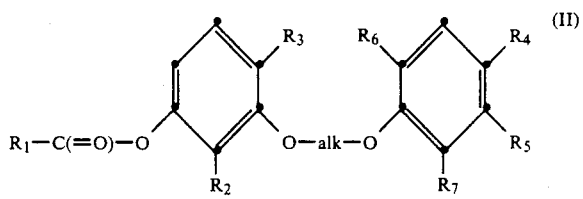

or b) reacting a compound of the formula

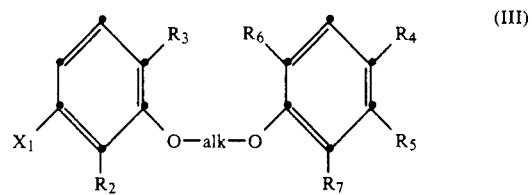

in which $X_1$ is free or etherified hydroxyl, with a compound the formula $R_1—X_2$ (IV), in which $X_2$ is free or functionally modified carboxyl, or c) converting $X_3$ in a compound of the formula

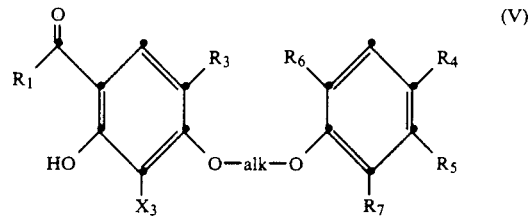

in which $X_3$ is a radical which can be converted into the fluorinated lower alkyl radical $R_2$, or in a salt thereof, into fluorinated lower alkyl $R_2$, or d) converting $X_4$ in a compound of the formula

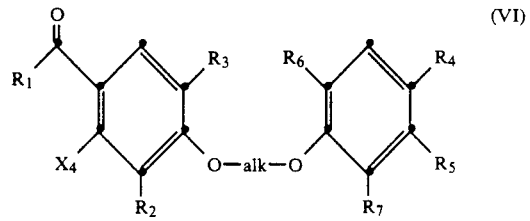

in which $X_4$ is a radical which can be converted into hydroxyl, into hydroxyl, or e) reacting compounds of the formulae

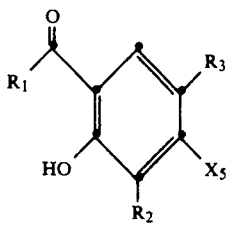

and

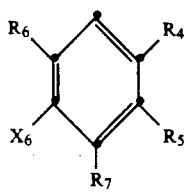

in which one of the radicals $X_5$ and $X_6$ is hydroxyl which is free or in salt form and the other is a radical —O—alkH substituted by reactive esterified hydroxyl or epoxy, i.e. an alkoxy radical corresponding to alk and substituted by reactive esterified hydroxyl, a mono-, di- or trioxaalkyl radical corresponding to alk or an alkoxy or mono- or dioxaalkylene radical corresponding to alk and substituted by epoxy, with one another, or f) reacting a compound of the formula

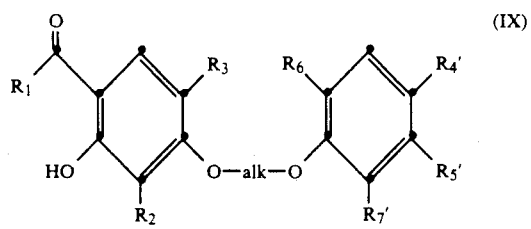

in which one of the radicals $R_4'$, $R_5'$ and $R_7'$ is the amino group, a radical $R_4'$ or $R_5'$ which differs from this is a radical $R_9$ and a radical $R_7'$ which differs from this is a radical $R_{10}$, or a salt thereof, with a compound of the formula $$X_7\text{—}R_8' \qquad (X)$$

in which $R_8'$ is a carboxyl group which is free, esterified or amidated or 5-tetrazolyl which is protected, if appropriate, in the 1-position and $X_7$ is a carboxyl group which is free, esterified, amidated, converted into an anhydride or, if $R_8'$ is 5-tetrazolyl protected in the 1-position, in salt form, and, if appropriate, detaching the protective group in the 1-position of a tetrazolyl group $R_8$, or g) converting $X_8$ is a compound of the formula

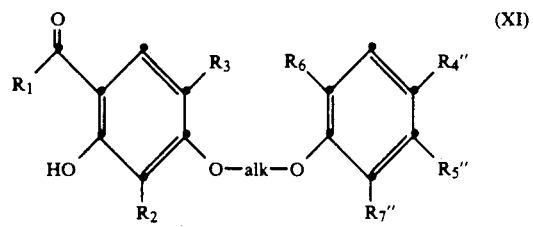

in which one of the radicals $R_4''$, $R_5''$ and $R_7''$ is a radical $X_8$, a radical $R_4''$ or $R_5''$ which differs from this is a radical $R_9$ and a radical $R_7''$ which differs from this is a radical $R_{10}$ and $X_8$ is a radical which can be converted into the desired group of the formula —NH—C(=O)—R_8, into this group, or h) converting alk' in a compound of the formula

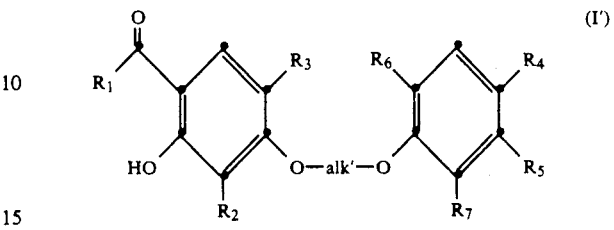

in which alk' is a radical which can be converted into a group alk, into a group alk, and, if desired, in each case converting a compound obtainable according to the process into another compound of the formula I, separating an isomer mixture obtainable according to the process and isolating the desired isomer(s), and/or converting a free compound obtainable according to the process into a salt or salt obtainable according to the process into the free compound or into another salt.

Free or etherified hydroxyl $X_1$ in formula III is, for example, lower alkoxy, such as methoxy.

Free or functionally modified carboxyl $X_2$ in formula IV is, for example, carboxyl which is free, esterified or converted into an anhydride, such as carboxyl, lower alkoxycarbonyl, for example methoxy- or ethoxycarbonyl, halogenocarbonyl, for example chlorocarbonyl, or carboxyl converted into an anhydride, of the formula —C(=O)—O—C(=O)—R_1 (Iva).

Radicals $X_3$ in formula V which can be converted into fluorinated lower alkyl radicals $R_2$ are, for example, fluorinated lower alkenyl radicals, such as 3-fluoro-, 3,3-difluoro- or 3,3,3-trifluoro-prop-1-enyl or 3-fluoro- or 3,3-difluoro-prop-2-enyl, fluorinated lower alkinyl radicals, such as 3-fluoro-, 3,3-difluoro- or 3,3,3-trifluoro-prop-1-ynyl, and furthermore fluorinated hydroxy-lower alkyl radicals, such as 3-fluoro-, 3,3-difluoro- or 3,3,3-trifluoro-1-hydroxy-propyl, and furthermore halogen with an atomic number of 19 to not more than 53, such as bromine or iodine, and furthermore chlorine.

Radicals $X_4$ in formula VI which can be converted into hydroxyl are, for example, etherified or esterified hydroxyl groups. Etherified hydroxyl $X_4$ is, for example, aliphatically etherified hydroxyl, for example lower alkoxy, such as methoxy, or lower alkenyloxy, such as allyloxy, phenyl-lower alkoxy, in particular substituted or unsubstituted phenyl-lower alkoxy, such as benzyloxy, and furthermore tetrahydropyran-2-yloxy or silyloxy, in particular tri-lower alkylsilyloxy, for example trimethylsilyloxy. Esterified hydroxyl $X_4$ is, for example, hydroxyl esterified with a carboxylic acid, such as an aliphatic or aromatic carboxylic acid, or with an aliphatic or aromatic half-ester of carbonic acid, such as lower alkanoyloxy, for example acetoxy, substituted or unsubstituted benzoyloxy, for example of the formula $R_1$—C(=O)—O—, halogenated or non-halogenated lower alkoxycarbonyl, for example methoxy-, ethoxy- or tertiary butoxycarbonyl, 2,2,2-triiodoethoxy- or 2,2,2-trichloroethoxycarbonyl, substituted or unsubstituted phenyl-lower alkoxycarbonyl, in particular 1-phenyl-lower alkoxycarbonyl, for example benzyloxycarbonyl, or substituted or unsubstituted phenoxycarbonyl.

Hydroxyl $X_5$ in the formula VII or $X_6$ in formula VIII or carboxyl in formula X, in salt form, is, in particular, in the form of an alkali metal salt, for example as the sodium or potassium salt.

Alkoxy radicals $X_5$ in formula VII and $X_6$ in formula VIII which are substituted by reactive esterified hydroxyl or epoxy are, for example, radicals of the formulae

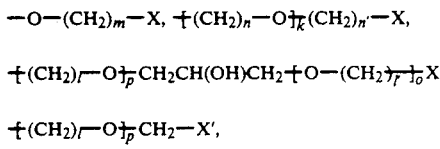

in which X is reactive esterified hydroxyl and X' is 1,2-epoxyethyl. Reactive esterified hydroxyl here is, for example, halogen, such as chlorine, bromine or iodine, or organic sulfonyloxy, such as lower alklanesulfonyloxy, for example methanesulfonyloxy, or substituted or unsubstituted benzenesulfonyloxy, for example benzene-, p-bromobenzene- or p-toluenesulfonyloxy.

Carboxyl $X_7$ in formula X which is free, esterified, amidated or converted into an anhydride is, for example, free carboxyl, esterified carboxyl $R_8$ or carboxyl esterified with a substituted or unsubstituted phenol, such as phenoxy-, 4-nitrophenoxy- or 2,4-dinitrophenoxycarbonyl, amidated carboxyl $R_8$ or activated carbamyl, such as 1-imidazolyl- or 1-(2,5-dimethylimidazolyl)-carbonyl, or carboxyl converted into an anhydride with a hydrogen halide acid, such as halogenocarbonyl, for example of the formula Hal—C(=O)—, in which Hal is chlorine, bromine or iodine, in particular chlorine.

Starting substances X are, in particular, those of the formulae $R_8''$-$R_8''$ (Xa), in which $R_8''$ is free or esterified carboxyl, and Hal—C(=O)—$R_8'$ (Xb). 5-Tetrazolyl radicals $R_8'$ in protected form are, for example, 1-(α-aralkyl)-tetrazol-5-yl radicals which are unsubstituted or substituted in the aryl part, such as 1-benzyltetrazol-5-yl or 1-(p-methoxybenzyl)-tetrazol-5-yl.

A radical $X_8$ in formula XI which can be converted into the group of the formula —NH—C(=O)—$R_8$ is, for example, a radical which can be converted into this group by solvolysis, i.e. hydrolysis, alcoholysis (reaction with the alcohol corresponding to the desired esterified carboxyl group $R_8$) and/or aminolysis (reaction with ammonia or an amine corresponding to the desired amidated carboxyl group $R_8$), for example a group of the formula —NH—$X_A$, in which $X_A$ is a functionally modified oxalo group which is other than a free, esterified or amidated oxalo group and can be converted into this. Such functionally modified oxalo groups are preferably those which contain, as the functionally modified α-carbonyl grouping, thioxomethylene, iminomethylene or an esterified and/or etherified dihydroxymethylene grouping, and/or, as the functionally modified carboxyl group, a functionally modified carboxyl group other than an esterified or amidated carboxyl group. Esterified and/or etherified dihydroxymethylene groupings are, for example, dihydroxymethylene groupings esterified with a hydrogen halide acid, such as hydrochloric acid, and/or etherified with a lower alkanol, such as methanol or ethanol. Examples are, in particular, dihalogenomethylene groupings, such as dichloromethylene, lower alkoxyhalogenomethylene groupings, such as methoxy- or ethoxychloromethylene, or di-lower alkoxymethylene groupings, such as dimethoxy- or diethoxymethylene. Functionally modified carboxyl groupings other than esterified or amidated carboxyl groups are, for example, the cyano group, carboxyl groups converted into anhydrides, such as halogenocarbonyl, for example chlorocarbonyl, imino ester groupings, such as imide- or amine halide groupings, for example iminochloro- or aminodichloromethyl, iminoether groupings, such as lower alkyl- or lower alkyleneiminoether groupings, for example methoxy- or ethoxyiminomethylene, 4,4- or 5,5-dimethyloxazolin-2-yl or 4,4,6-trimethyl-dihydro-oxazin-2-yl, amidino groups, such as amidino or lower alkylamidino, for example methylamidino, orthoacid groupings esterified with a hydrogen halide acid, such as hydrochloric acid, and/or etherified with a lower alkanol, such as tri-lower alkoxy-, lower alkoxyhalogeno- or trihalogenomethyl groups, in particular trimethoxy- or triethoxymethyl, ethoxydichloromethyl or trichloromethyl, or free or esterified thiocarboxyl groups, such as lower alkylthiocarbonyl groups, for example ethylthiocarbonyl.

A radical $X_8$ which can be converted into the group of the formula —NH—C(=O)—$R_8$, in which $R_8$ is 5-tetrazolyl, is, for example, the group of the formula —NH—C(=O)—CN or a group of the formula —NH—C(=O)—$R_8'$, in which $R_8'$ is 5-tetrazolyl protected in the 1-position. 5-Tetrazolyl radicals $R_8'$ in the protected form are, for example, 1-(α-aralkyl)-tetrazol-5-yl radicals which are unsubstituted or substituted in the aryl part, such as 1-benzyltetrazol-5-yl or 1-(p-methoxybenzyl)-tetrazol-5-yl.

Other radicals $X_8$ which can be converted into groups of the formula —NH—C(=O)—$R_8$ are, for example, groups of the formula —NH—$X_B$ which can be converted oxidatively into these, in which $X_B$ is the hydrated or non-hydrated glyoxyl group which can be converted oxidatively into the oxalo group of the formula —C(=O)—$R_8$, in which $R_8$ is carboxyl. This can advantageously be formed in situ in the course of the oxidation reaction, for example from the acyl group of an aliphatic or araliphatic carboxylic acid, which may be α,β-unsaturated or α,β-dihydroxylated, a glycoloyl group which is free or esterified on the hydroxyl group or the glycyl group, or liberated from one of its functional derivatives, for example one of its acetals or imines. Acyl groups of carboxylic acids which may be α,β-unsaturated or α,β-dihydroxylated are, for example, alkanoyl groups, such as lower alkanoyl, for example acetyl, acyl groups of α,β-unsaturated aliphatic mono- or dicarboxylic acids, for example acryloyl or crotonyl, or the acyl group of free or functionally modified fumaric or maleic acid, acyl groups of α,β-unsaturated araliphatic carboxylic acids, for example substituted or unsubstituted cinnamoyl, or acyl groups of aliphatic α,β-dihydroxydicarboxylic acids, such as tartaric acid, or monofunctional carboxyl derivatives, such as esters or amides, thereof. Esterified glycoloyl groups are, for example, glycoloyl groups esterified on the hydroxyl group with a mineral acid, such as a hydrogen halide acid, for example with hydrochloric or hydrobromic acid, or with a carboxylic acid, for example with acetic acid or substituted or unsubstituted benzoic acid. Acetalised glyoxyloyl groups are, for example, glyoxyloyl groups acetalised with lower alkanols or a lower alkanediol, such as dimethoxy-, diethoxy- or ethylenedioxyacetyl. Imines of glyoxyloyl groups are, for example, substituted or unsubstituted N-benzylimines or N-(2-benzothiazolyl)-imines thereof or imines with 3,4-di-tert.-butyl-o-quinone. Other radicals which can be converted oxidatively into the oxalo group are, for example, 2-furoyl groups which are substituted or unsubstituted, such as those containing an acetalised formyl group, such as diethoxymethyl, in the 5-position. Groups which can be oxidised to esterified oxalo groups of the formula —C(=O)—R$_8$ in which R$_8$ is esterified carboxyl are etherified glycoloyl groups, such as lower alkoxyacetyl. Radicals X$_B$ which can be oxidised to free, esterified or amidated oxaloamino groups are, furthermore, free, hydrated or acetalised formylmethylamino groups or free or functionally modified carboxymethylamino groups or carboxymethyleneimino groups, for example of the formula —NH—CH$_2$—CH=O, —NH—CH$_2$—R$_8$ or —N=CH—R$_8$.

Groups which can be converted into radicals alk are, for example, radicals alk substituted by oxo or etherified or esterified hydroxyl, such as oxoalkylene, oxo(oxa)alkylene or oxo(dioxa)alkylene radicals, for example of the formula

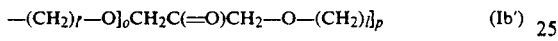

or etherified or esterified hydroxyalkylene, hydroxy(oxa)alkylene or hydroxy(dioxa)alkylene radicals of the formula

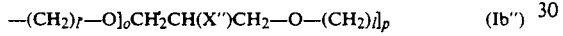

in which X″ is etherified or esterified hydroxyl.

Etherified hydroxyl X″ here is, for example, hydroxyl etherified with an α-aralkanol or a silanol, such as substituted or unsubstituted benzyloxy or tri-lower alkylsilyloxy, for example trimethylsilyloxy.

Esterified hydroxyl X″ is, for example, hydroxyl esterified with a carboxylic acid, such as a lower alkanoic acid, or a half-ester of carbonic acid, such as lower alkanoyloxy, for example acetoxy or pivaloyloxy, lower alkoxycarbonyloxy, for example tertiary butoxycarbonyloxy, or substituted or unsubstituted benzyloxycarbonyl, for example carbobenzoxy.

The reactions according to the process and the preparation of novel starting substances and intermediates are carried out by procedures analogous to those for the reaction and formation of known starting substances and intermediates. The particular customary auxiliaries, such as catalysts, condensing and solvolysis agents and/or solvents or diluents, and reaction conditions, such as temperature and pressure conditions, and, if appropriate, protective gases are used here, even if this is not expressly mentioned below.

The rearrangement of compounds II according to process variant a) is carried out, for example, photochemically or in the presence of an acid condensing agent. Suitable acid condensing agents are, for example, Lewis acids, in particular complex metal halides of the formula M$^n$Y$_n$ (XIX), in which M is an n-valent, coordinatively unsaturated metal atom of group IIb, IIIa, IIIb, Iva, Ivb, Va or VIIIb of the periodic table of the elements, for example a zinc$^{II}$, boron$^{III}$, aluminium$^{III}$, gallium$^{III}$, tin$^{IV}$, titanium$^{IV}$, antimony$^V$ or iron$^{III}$ atom, and Y is a halogen atom, in particular with an atomic number of not more than 35, such as fluorine, chlorine or bromine. Boron trifluoride, aluminium trichloride, gallium chloride, tin tetrachloride or, in particular, zinc chloride is preferably used. Other suitable acid condensing agents are complex oxygen acids, in particular of sulfur or phosphorus, such as sulfuric acid, pyrosulfuric acid, phosphoric acid, pyrophosphoric acid or polyphosphoric acid. Suitable inert solvents are, for example, carbon tetrachloride, tetrachloroethane, trichloroethylene, carbon disulfide and nitrobenzene. If necessary, the reaction is carried out with cooling or warming, for example at about −10° to about 40° C., in particular at +5° to +30° C.

Starting substances II can be prepared, for example, by reacting compounds of the formulae

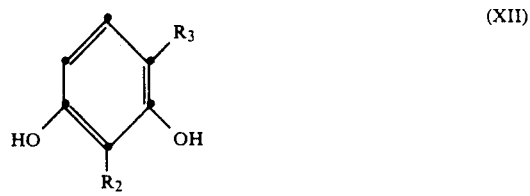

and

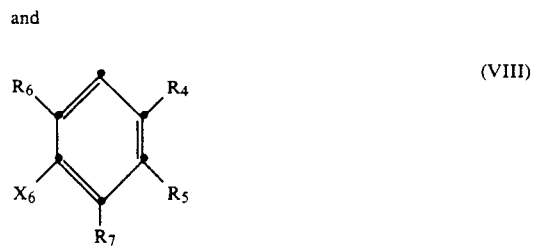

in which X$_6$ is an alkoxy radical substituted by reactive esterified hydroxyl or epoxy, for example of the formula

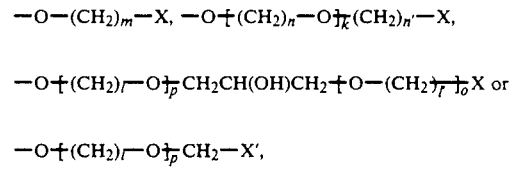

in which X is reactive esterified hydroxyl, for example halogen, and X′ is 1,2-epoxyethyl, with one another in the customary manner and O-acylating the reaction product of the formula

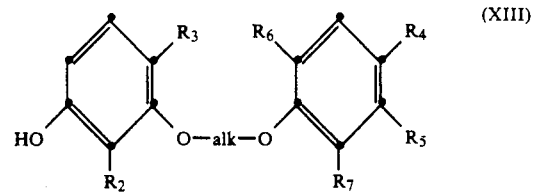

in the customary manner, for example by reaction with a compound R$_1$-X$_1$ (IV), in which X$_1$ is, for example, halogenocarbonyl or carboxyl converted into an anhydride, of the formula —C(=O)—O—C(=O)—R$_1$.

Compounds XII are obtained, for example, by reacting compounds of the formulae

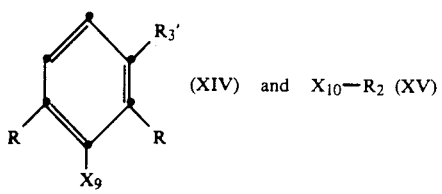

(XIV) and X$_{10}$—R$_2$ (XV)

in which the radicals R are identical or different etherified hydroxyl groups, R$_3$' is hydrogen, lower alkoxy, trifluoromethyl, fluorine or nitro and one of the groups X$_9$ and X$_{10}$ is a metallic radical, such as an alkali metal atom, for example sodium or lithium, or furthermore copper, or a halogenoalkaline earth metal group, for example of the formula —Mg—Hal, and the other is a group —Hal, which is halogen, for example bromine or iodine, with one another, for example in a di-lower alkyl or lower alkylene ether, such as diethyl ether, tertiary butoxymethane, dioxane or tetrahydrofuran, reducing nitro R$_3$' to amino and converting this into halogen R$_3$ by treatment with sodium nitrite and a hydrogen halide acid, and splitting the groups R, for example by treatment with hydrogen bromide in methylene chloride, to give hydroxyl In a modification of this process, the organometallic component can be formed in situ by using the corresponding halogen compound as the starting substance and carrying out the reaction, preferably with warming, in the presence of the corresponding metal in finely divided form, for example in the form of copper powder. In another modification of this process, bis-ether derivatives of compounds XII are obtained by reacting a compound XIV in which X$_9$ is one of the metallic radicals mentioned, preferably an alkali metal atom or a group —Mg—Hal, with a fluorinated lower alkanal or lower alkanone, hydrogenating the hydroxy-lower alkyl group in the compound formed, of the formula

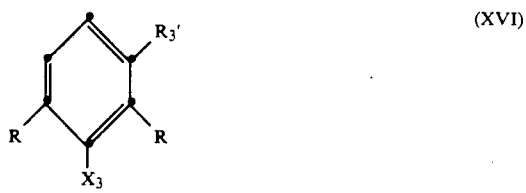

in which X$_3$ is fluorinated hydroxy-lower alkyl, if appropriate after detachment of water, for example by acetylation and subsequent treatment with zinc and ammonium chloride, to the corresponding fluorinated lower alkenyl group, to give the desired fluorinated radical R$_2$, converting nitro into halogen and splitting R to give hydroxyl.

In another modification of this process, it is also possible to react the compound XIV, in which X$_9$ is bromine or iodine, with trifluoroiodomethane in the presence of copper powder to give the corresponding compound of the formula

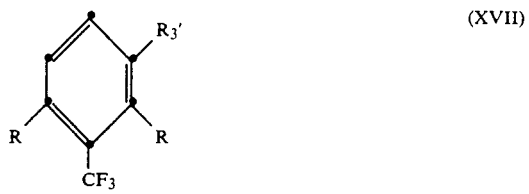

and subsequently, if appropriate, to convert nitro into halogen and the radicals R into hydroxyl.

Compounds XII in which R$_2$ is 3-fluoro- or 3,3-difluoropropyl are obtained in a particularly elegant manner by subjecting a compound of the formula

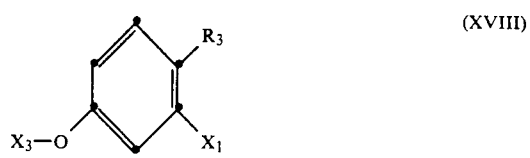

in which X$_1$ is free or etherified hydroxyl and X$_3$ is a 1-fluoro- or 1,1-difluoroprop-2-enyl radical, which in turn is obtainable by reaction of the corresponding R$_3$-resorcinol or resorcinol monoether with a 1-fluoro- or 1,1-difluorolower alkyl bromide, to allyl rearrangement, for example by heating to about 150° to 250° C., preferably to about 190° to 220° C., advantageously in a solvent, such as diphenyl ether or N,N-dimethyl- or N,N-diethylaniline, and hydrogenating the 3-fluoro- or 3,3-difluoroprop-2-enyl group formed in the reaction product of the formula

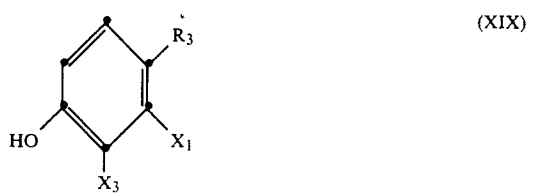

into 3-fluoro- or 3,3-difluoro-propyl and, if necessary, splitting etherified hydroxyl X$_1$ to give hydroxyl.

Compounds XII in which R$_2$ is 3,3,3-trifluoropropyl are obtained in a particularly elegant manner according to a novel procedure by reacting an aldehyde of the formula

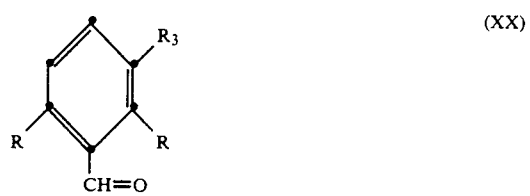

in which R is, for example, methoxy, with the compound of the formula CF$_3$CCl$_2$ZnCl(C$_2$H$_5$)$_2$O (XXI), for example in the presence of dimethylformamide, to give the corresponding compound of the formula

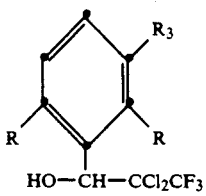

(XXII)

acylating this in the side chain, for example by reaction with acetic anhydride in the presence of pyridine, converting the reaction product of the formula

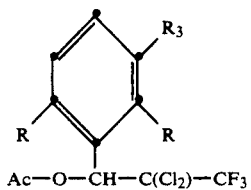

(XxIIa)

in which Ac is acyl, for example acetyl, into the corresponding compound of the formula

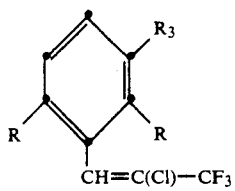

(XXIII)

by treatment with a metallic reducing agent, for example with activated zinc dust in the presence of ammonium chloride, detaching hydrogen chloride from this product, for example by treatment with potassium tertiary butanolate, hydrogenating the side chain in the resulting compound of the formula

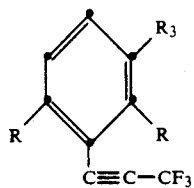

(XXIV)

for example in the presence of palladium-on-charcoal, and liberating the hydroxyl groups in the resulting compound of the formula

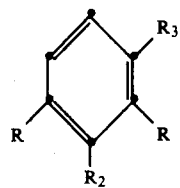

(XXV)

for example by treatment with hydrobromic acid in methylene chloride.

The preparation of compounds VIII is described under process variant e).

The reaction of compounds III and IV of which those in which $X_2$ is carboxyl are particularly suitable, according to process variant b) is usually carried out in the presence of an acid condensing agent, advantageously in an inert solvent, if necessary with cooling or heating, for example at about $+80°$ to $+140°$ C., in particular at about 80° to about 120° C. Acid condensing agents are, for example, those mentioned for process variant a).

Starting substances III can be prepared, for example, by reacting compounds of the formulae

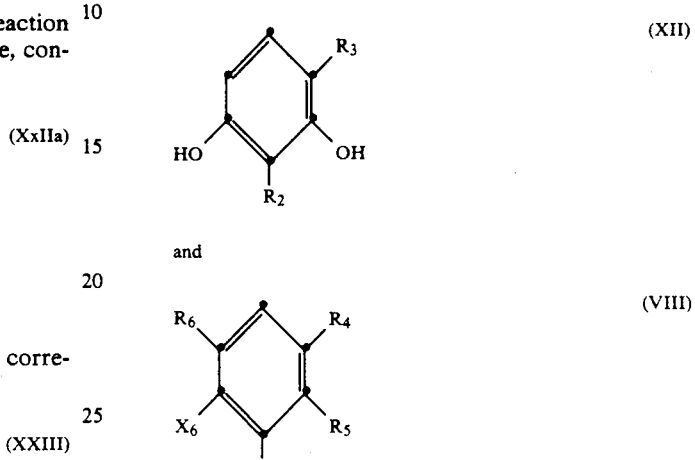

with one another, it also being possible for the compound XII to be in monoether and/or in salt form, and $X_6$ being a radical —O—alkH substituted by reactive esterified hydroxyl, i.e. a reactive esterified hydroxyalkoxy radical or an epoxy-alkoxy radical, for example a group of the formula

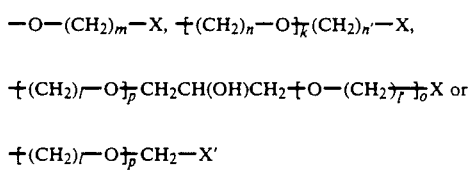

in which X is reactive esterified hydroxyl, such as halogen, and X' is 1,2-epoxyethyl. The reaction is carried out, for example, analogously to that in process variant e).

The conversion of the above radicals $X_3$ containing fluorine to groups $R_2$ according to process variant c) is carried out, for example, by reduction. The reducing agent is, for example, hydrogen in the presence of a hydrogenation catalyst, such as a platinum, palladium or rhodium catalyst, for example platinum oxide. The treatment with catalytically activated hydrogen (hydrogenation) is carried out under normal or at most slightly increased pressure and temperature conditions, for example under an increased pressure of about 0 to 5 bar and/or in the temperature range from about 20° to about 80° C. The conversion of halogen into, for example, trifluoromethyl, is carried out, for example, by heating with trifluoroiodomethane and copper powder.

Starting substances V in which $X_3$ is a mono- or difluorinated lower alkenyl radical are obtained, for example, by subjecting a compound of the formula

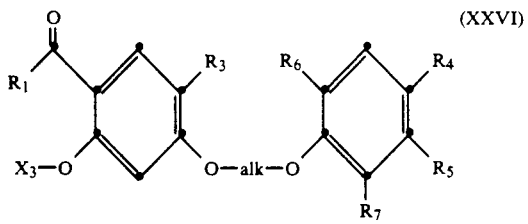

(XXVI)

to allyl rearrangement, for example by heating to about 150° to 250° C., preferably to about 190° to 220° C., advantageously in a solvent, such as diphenyl ether or N,N-dimethyl- or N,N-diethylaniline.

Compounds XXVI are in turn obtained by reacting a corresponding compound of the formula

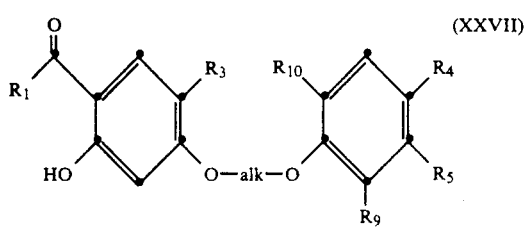

(XXVII)

with a fluorinated lower alkene of the formula $X_3$—H (XXVIII) substituted by chlorine, bromine or iodine in the allyl position relative to the double bond, for example in the presence of a basic condensing agent, such as potassium carbonate.

The conversion of groups $X_4$ into hydroxyl according to process variant d) is carried out in the customary manner, for example by treatment with a complex metal halide of the formula $M^nY_n$ (XIX), in which M is an n-valent, coordinatively unsaturated metal cation of group IIa, IIb, IIIa, IIIb, Iva, Ivb, Va or VIIIb of the periodic table of the elements, for example a magnesium, zinc$^{II}$, boron$^{III}$, aluminium$^{III}$, gallium$^{III}$, tin$^{IV}$, titanium$^{IV}$, antimony$^V$ or iron$^{III}$ or iron$^{VI}$ ion, and Y is a halogen atom with an atomic number or not more than 35, such as fluorine or chlorine, for example aluminium trichloride, or with a tertiary organic ammonium salt, such as a pyridinium or tri-lower alkylammonium halide, for example with pyridinium chloride or bromide or triethylammonium chloride, but can also be carried out by solvolysis, in particular by hydrolysis, if necessary in the presence of a, preferably acid, hydrolysing agent. In addition to customary basic hydrolysing agents, such as alkali metal hydroxides, hydrolysing agents are, as acid hydrolysing agents, for example, mineral acids, for example hydrochloric, hydrobromic or hydriodic acid, sulfuric acid, phosphoric acid or polyphosphoric acid, and also complex metal acids, for example hexachloroantimonic acid, tetrafluoboric acid and the like, and in the case of hydroxyl groups $X_4$ esterified with organic carboxylic acids, furthermore lower alkanecarboxylic acids, such as acetic acid. Solvents in the hydrolysis are, for example, water-miscible organic solvents. The reaction is in each case preferably carried out in the presence of a solvent or diluent or a solubilising agent, with cooling or warming, for example in the temperature range from about 0° to 120° C., and/or under an inert gas.

In compounds VI which contain, as group $x_4$, a substituted or unsubstituted α-phenyl-lower alkoxy group or another customary protected hydroxyl group which can be split by reduction, the hydroxyl group can advantageously be liberated by reduction. Thus, for example, it is possible to carry out hydrogenation, i.e. reduction with hydrogen in the presence of a hydrogenation catalyst, for example a palladium, platinum, nickel or rhodium catalyst, for example palladium-on-charcoal or Raney nickel.

Furthermore, starting from compounds VI in which $x_4$ is hydroxyl esterified with an organic carboxylic acid, the hydroxyl group can be liberated by transesterification, i.e. by treatment with an alcohol, for example a lower alkanol, in the presence of an acid or basic agent, such as a mineral acid, for example sulfuric acid, or an alkali metal hydroxide or alcoholate, for example sodium hydroxide or a sodium lower alkanolate.

Starting substances VI are prepared, for example, by reacting compounds of the formulae

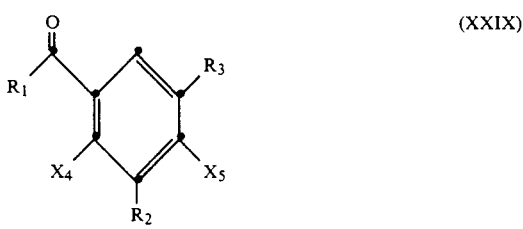

(XXIX)

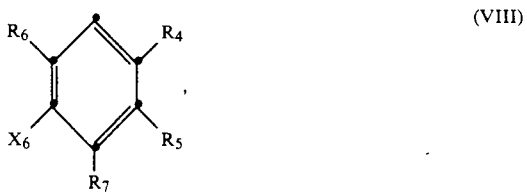

(VIII)

in which one of the radicals $X_5$ and $X_6$ is hydroxyl which is free or in salt form and the other is a radical —O—alkH which is substituted by reactive esterified hydroxyl or epoxy, for example a group of the formula

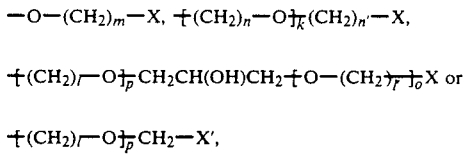

in which X is reactive esterified hydroxyl, for example halogen, and X' is 1,2-epoxyethyl, with one another.

The reaction of compounds VII and VIII according to process variant e) is carried out in the customary manner, for example in the presence of a basic condensing agent, such as a hydroxide or carbonate of an alkali metal or alkaline earth metal, such as sodium hydroxide or potassium hydroxide or potassium carbonate or calcium carbonate, advantageously in a lower alkanol, for example methanol or amyl alcohol, di-lower alkyl ketone, for example in acetone or diethyl ketone, or N,N-di-lower alkyl-lower alkanoic acid amide or N-lower alkyl-lower alkanoic acid lactam, for example in dimethylformamide or N-methylpyrrolidinone.

The starting substances VII are prepared, for example, by reacting a compound of the formula

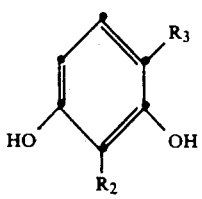

(XII)

with a compound of the formula $R_1$—$X_2$ [IV; $X_2$=carboxyl] in the presence of a Lewis acid, for example zinc chloride, and, if desired, converting the hydroxyl group in the p-position relative to $R_1$—C(=O)— in the resulting compound VII, in which $X_5$ is hydroxyl, into an alkoxy radical substituted by halogen or hydroxyl by reaction with a dihalogenoalkane, epoxyalkane or halogenoalkanol and, if appropriate, reactively esterifying hydroxyalkoxy, for example by treatment with thionyl chloride, phosphorus tribromide or a sulfonic acid chloride.

Compounds VIII can be obtained, for example, by reducing the nitro group in a compound of the formula

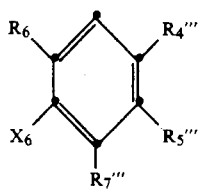

(XXX)

in which one of the radicals $R_4'''$, $R_5'''$ and $R_7'''$ is the nitro group, a radical $R_4'''$ or $R_5'''$ which differs from this is a radical $R_9$ and a radical $R_7'''$ which differs from this is a radical $R_{10}$, to amino, for example with hydrogen in the presence of Raney nickel, and reacting the compound of the formula

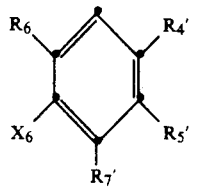

(XXXI)

in which one of the radicals $R_4'$, $R_5'$ and $R_7'$ is the amino group, a radical $R_4'$ or $R_5'$ which differs from this is a group $R_9$ and a radical $R_7'$ which differs from this is a radical $R_{10}$, with a compound of the formula Hal—C(-=O)—$R'_8$ (Xb; Hal = halogen) in the presence of a base, for example triethylamine or pyridine, and, if desired, converting the hydroxyl group in the resulting compound VIII, in which $X_6$ is hydroxyl, into an alkoxy radical substituted by halogen, epoxy or hydroxyl by reaction with a dihalogenoalkane, epoxyalkane or halogenoalkanol, dihalogeno(hydroxy)alkane, halogeno(epoxy)alkane or halogenoalkanediol, and, if appropriate, reactively monoesterifying hydroxyalkoxy or dihydroxyalkoxy, for example by treatment with thionyl chloride, phosphorus tribromide or a sulfonic acid chloride.

The reaction of compounds IX and X according to process variant f) can be carried out in the customary manner, in particular in the manner known from the literature for analogous reactions, if necessary in the presence of a condensing agent, in the case of reaction with an ester-halide or amide-halide of oxalic acid, for example, a basic condensing agent, such as a tertiary organic nitrogen base, for example triethylamine or pyridine, or an alkali metal hydroxide or carbonate, for example sodium hydroxide or potassium hydroxide, or in the case of the reaction with oxalic acid, for example, a condensing agent which effects dehydration of the ammonium salt primarily formed, such as a water-binding agent, for example dicyclohexylcarbodiimide or an isonitrile, such as tertiary butylisonitrile, or a mineral acid, for example hydrochloric acid, or an acid anhydride, for example phosphorus pentoxide, in each case in an inert solvent, such as a halogenoalkane, for example in methylene chloride, or an N,N-dialkylamide, for example in N,N-dimethylformamide or -acetamide.

The 1-protective group of 5-tetrazolyl radicals $R'_8$ can then be detached, for example, by acidolysis, i.e. treatment with an acid, for example with trifluoroacetic acid/anisole, or hydrogenolytically, in particular by means of hydrogen and palladium-on-charcoal.

Starting substances IX can be prepared, for example, by reacting compounds of the formulae

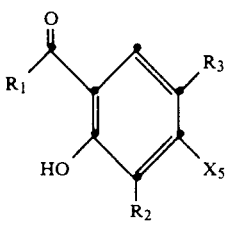

(VII)

and

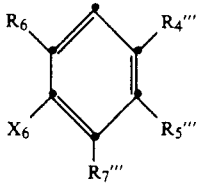

(XXX)

in which one of the radicals $R_4'''$, $R_5'''$ and $R_7'''$ is the nitro group, a radical $R_4'''$ or $R_5'''$ which differs from this is a radical $R_9$ and a radical $R_7'''$ which differs from this is a radical $R_{10}$, and in which one of the radicals $X_5$ and $X_6$ is hydroxyl which is free or in salt form and the other is a radical —O—alkH substituted by reactive esterified hydroxyl or epoxy, for example a group of the formula

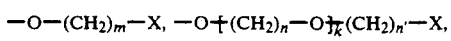

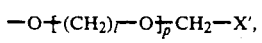

in which X is reactive esterified hydroxyl, for example halogen, and X' is 1,2-epoxyethyl, with one another, and reducing the nitro group in the resulting compound of the formula

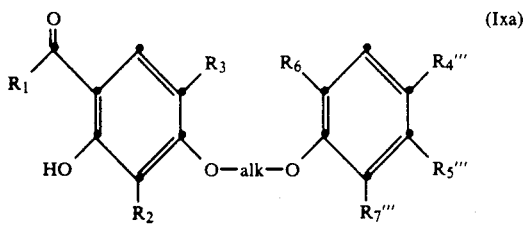

(Ixa)

to amino, for example by reaction with hydrogen in the presence of a hydrogenation catalyst, such as palladium-on-charcoal or, in particular, Raney nickel, for example in tetrahydrofuran.

Conversion of the group $X_8$ in compounds XI into those of the formula —NH—C(=O)—$R_8$ according to process variant g) is carried out, for example, by solvolysis or oxidation or, starting from groups $X_8$ of the formula —NH—C(=O)—CN, by reaction with hydrazoic acid, or, starting from groups $X_8$ of the formula —NHC(=O)—$R_8'$, in which $R_8'$ is 5-tetrazolyl protected in the 1-position, by detachment of the protective group. Thus, the groups $X_A$ mentioned in radicals $X_8$ of the formula —NH—$X_A$ can be converted hydrolytically into the oxalo group. A group $X_A$ containing, as a functionally modified carboxyl group, an iminoether, orthoester or ester-halide grouping and/or, as a functionally modified α-carbonyl group, thioxo- or iminomethylene or an esterified or etherified dihydroxymethylene group can furthermore be hydrolysed to esterified oxalo groups —C(=O)—$R_8$. A group $X_A$ containing, as a functionally modified carboxyl group, the cyano group or an amidino or imide- or amide-halide grouping and/or, as a functionally modified α-carbonyl group, thioxo- or iminomethylene or an etherified or esterified dihydroxymethylene group, can likewise be hydrolysed to amidated oxalo groups —C(=O)—$R_8$. The hydrolysis can be carried out in the customary manner, if necessary in the presence of a basic or, preferably, acid hydrolysing agent, such as an alkali metal hydroxide, such as sodium or potassium hydroxide, or, preferably, a proton acid, preferably a mineral acid, for example a hydrogen halide acid, such as hydrochloric acid, or an organic carboxylic or sulfonic acid, for example acetic acid or p-toluenesulfonic acid.

A functionally modified oxalo group $X_A$ containing, as a functionally modified carboxyl group, a carboxyl group converted into an anhydride, such as halogenocarbonyl, for example chlorocarbonyl, or cyanocarbonyl, or a lower alkyleneimino-ether grouping, for example 4,4- or 5,5-dimethyloxazolin-2-yl, or 4,4,6-trimethyl-dihydro-oxazin-2-yl, can furthermore be converted into esterified oxalo groups —C(=O)—$R_8$ by customary alcoholysis, i.e. reaction with the corresponding alcohol. Alcoholysis of carboxyl groups converted into anhydrides is advantageously carried out in the presence of a basic condensing agent, for example pyridine or triethylamine, whilst alcoholysis of carboxyl or a lower alkyleneiminoether grouping is preferably carried out under acid conditions, for example in the presence of hydrochloric acid, p-toluenesulfonic acid or acetic acid. A functionally modified oxalo group containing a carboxyl group converted into an anhydride can also be converted into an amidated oxalo group —C(=O)—$R_8$ in an analogous manner by ammonolysis or aminolysis, i.e. reaction with ammonia or a corresponding primary or secondary amine, preferably in the presence of a basic condensing agent, for example sodium hydroxide, pyridine or triethylamine.

The groups $X_B$ mentioned are converted into those of the formula —NH—C(=O)—$R_8$, for example, by oxidation. The oxidation can be carried out in the customary manner by reaction with a suitable oxidising agent. Suitable oxidising agents are, in particular, oxidising heavy metal compounds, such as silver compounds, for example silver nitrate or silver picolinate, oxygen acids of heavy metals, for example of manganese-IV, manganese-VII, chromium-VI and iron-III, or of halogens or anhydrides or salts thereof, such as chromic acid, chromium dioxide, potassium dichromate, potassium permanganate, manganese dioxide, potassium hexacyanoferrate, sodium chlorite in the presence of sulfamic acid, sodium hypochlorite in the presence of nickel chloride or sodium iodate, sodium periodate or lead tetraacetate. The reaction with these oxidising agents is carried out in the customary manner, for example in an inert solvent, such as acetone, acetic acid, pyridine or water, or in a, preferably aqueous, inert solvent mixture, at normal temperature or, if necessary, with cooling or warming, for example at about 0° to about 100° C. The oxidation of free or etherified glycoloyl groups to free or esterified oxalo groups is advantageously carried out, for example, with potassium permanganate in aqueous pyridine or acetone at room temperature. Acetalised glyoxyl groups and iminoacetyl groups are preferably oxidised under acid conditions, for example with potassium dichromate in sulfuric acid, acyl groups of α,β-dihydroxylated aliphatic carboxylic acids, such as the acyl radical of tartaric acid, are advantageously oxidised with periodic acid, whilst potassium ferrate in an alkaline medium, for example at pH 10–13, for example 11.5, or organic silver salts, such as silver picolinate, are preferably used for the oxidation of the glycyl group. Groups of the formula —N=CH—$R_8$ are preferably oxidised with an organic peracid, for example with peracetic acid or m-chloroperbenzoic acid, in an inert solvent, for example methylene chloride, chloroform or benzene.

The reaction of groups $X_8$ of the formula —NH—C(=O)—CN with hydrazoic acid is preferably carried out with formation of the acid in situ by treatment of an alkali metal azide with an acid, such as hydrochloric acid, preferably in toluene or similar solvents.

Detachment of the protective group from groups $X_8$ of the formula —NH—C(=O)—$R_8'$, in which $R_8'$ is 5-tetrazolyl protected in the 1-position, is carried out in the customary manner, in particular by acidolysis, i.e. treatment with an acid, for example with trifluoroacetic acid, in an ether, such as anisole, or by catalytic hydrogenation, for example in the presence of palladium.

The starting substances XI are prepared, for example, by reacting a compound of the formula

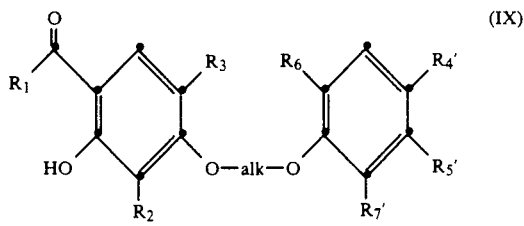

(IX)

in which one of the radicals $R_4'$, $R_5'$ and $R_7'$ is the amino group, a radical $R_4'$ or $R_5'$ which differs from this is a radical $R_9$ and a radical $R_7'$ which differs from this is a radical $R_{10}$, or an acid addition salt thereof, with a corresponding acid, for example of the formula $X_A$—OH (XXXIIa) or $X_B$—OH (XXXIIb) or $R_8'$—COOH (XXXIIc) or a functional derivative thereof. Functional derivatives of acids XXXIIa to XXXIIc are, in particular, acid derivatives containing a carboxyl group which is esterified, amidated or converted into an anhydride, such as lower alkoxycarbonyl, substituted or unsubstituted carbamyl, for example carbamyl or imidazol-1-yl-carbonyl, or halogenocarbonyl, for example chloro- or bromocarbonyl, or a group of the formula —$CON_3$ or —$CON_2^{\oplus}$ $Hal^{\ominus}$. Examples of acids XXXIIa to XXXIIc and functional derivatives thereof are, in particular: as functional derivatives of acids XXXIIa, oxalyl halides, such as oxalyl chloride or oxalyl bromide, tri-lower alkoxy- and dihalogeno-lower alkoxyacetic acid lower alkyl esters, such as tetraethyl oxalate or diethyl dichlorooxalate, oxalic acid iminodialkyl esters, such as mono- or diiminodiethyl oxalate, oxalic acid amidines, such as N-lower alkyloxalic acid esteramidines, oxalic acid dithio-lower alkyl esters, such as dimethyl ester, cyanoformyl chloride or cyanogen, and, as acids XXXIIb and functional derivatives thereof, glycolic acids and their lower alkyl esters and the corresponding lactide, mono- or di-lower alkoxyacetic acid lower alkyl esters, such as ethyl esters, for example ethyl ethoxy- or diethoxyacetate, halogenoacetic anhydrides, such as chloroacetic anhydride or chloroacetyl chloride and tartaric acid, or 2,3-diacetoxysuccinic anhydride, and furthermore cinnamoyl chloride, acetyl chloride and glycine. Functional derivatives of acids XXXIIc are, in particular, chlorides thereof.

The reaction of compounds IX and XXXIIa to XXXIIc or their derivatives can be carried out in the customary manner, for example in the presence of a water-binding agent, such as an acid anhydride, for example phosphorus pentoxide, or dicyclohexylcarbodiimide, or, for example, an acid or basic condensing agent, such as a mineral acid, for example hydrochloric acid, or an alkali metal hydroxide or carbonate, for example sodium or potassium hydroxide, or an organic nitrogen base, for example triethylamine or pyridine. In the case of the reaction with an acid anhydride, such as an acid chloride, an organic nitrogen base is preferably used as condensing agent 1. The reaction with carboxylic acids is preferably carried out in the presence of a water-binding agent If necessary, the reaction is in each case carried out in an inert solvent, at normal temperature or with cooling or warming, for example in a temperature range from about 0° to about 100° C., in a closed vessel and/or under an inert gas, for example nitrogen Compounds XI in which $X_8$ is a group $R_8$—CH=N— can be prepared analogously by condensation of compounds IX with free, esterified or amidated glyoxylic acid.

Compounds XI in which $X_8$ is a group —NH—$X_B$ and $X_B$ is glyoxyloyl can furthermore be prepared by heating a corresponding halogenoacetyl, such as bromoacetyl, compound with hexamethylenetetramine, preferably in an aqueous alcohol, or oxidising the starting compound with silver tetrafluoborate in dimethylsulfoxide. A chloroacetyl compound can also be oxidised analogously with potassium dichromate in hexamethylphosphoric acid triamide in the presence of dicyclohexyl-18-crown-6 ether. Compounds XI in which $X_8$ is a group —NH—$X_B$ and $X_B$ is an iminoacetyl group, for example substituted or unsubstituted benzyliminoacetyl, can be prepared starting from the corresponding glycyl compounds, by reacting these with the corresponding carbonyl compound, for example with benzaldehyde, and rearranging the intermediate thus obtainable, for example an N-benzylideneglycyl compound, preferably under the reaction conditions.

Functionally modified oxalo groups containing, as a functionally modified carboxyl group, an iminoether grouping can be prepared starting from the corresponding cyanocarbonyl compound by reaction with the corresponding alcohol, for example a lower alkane(-di)ol or amino-lower alkanol.

Conversion of the radical alk' of a compound I' according to process variant h) is carried out in the customary manner, for example reductively, starting from compounds I' in which alk' is a radical alk substituted by oxo or hydroxyl etherified with an α-alkanol or esterified with a carbonic acid mono-α-aralkyl radical, and solvolytically, starting from compounds IX in which alk' is a radical alk substituted by etherified or esterified hydroxyl groups other than those mentioned above.

Reducing agents for the reduction of radicals alk' substituted by oxo to the corresponding radicals alk substituted by hydroxyl are, for example, alkali metal borohydrides, such as lithium borohydride, sodium borohydride or sodium cyanoborohydride, or secondary alcohols, such as secondary lower alkanols or cyclo-lower alkanols, for example isopropanol or cyclohexanol, in the presence of an aluminium alcoholate, in particular isopropanol in the presence of aluminium isopropanolate. The reaction with the alkali metal borohydrides mentioned is advantageously carried out in a lower alkanol, a di-lower alkyl ether or a lower alkylene ether or mixtures of these solvents, for example in ethanol. The reaction with alcohols in the presence of an aluminium alcoholate is advantageously carried out in an excess of the alcohol used as the reducing agent.

Radicals alk' substituted by oxo can, however, also be reduced to the corresponding unsubstituted radicals alk' by replacing the oxo group by 2 hydrogen atoms, by reaction with hydrazine or semicarbazide and a base, for example an alkali metal lower alkanolate, such as sodium methanolate, or in a high-boiling alcohol, for example di- or triethylene glycol or diethylene glycol monomethyl ether, with hydrazine and an alkali metal hydroxide, such as potassium hydroxide, preferably with heating, for example at the boiling point. The corresponding hydrazones or semicarbazones are thereby intermediately formed However, the reaction can also be carried out with a sulfonic acid hydrazide, for example with p-toluenesulfonic acid hydrazide, to give the corresponding N'-sulfonylhydrazones, for example N'-(p-toluenesulfonyl)-hydrazones, and these can be reduced with an alkali metal borohydride, for example with lithium or sodium borohydride.

Reductive splitting of α-aralkoxy or α-aralkoxycarbonyloxy to hydroxyl is preferably carried out by hydrogenolysis, i.e. the action of hydrogen in the presence of a hydrogenation catalyst, such as a palladium, platinum, iridium or nickel catalyst, for example palladium-on-charcoal, platinum oxide or Raney nickel, advantageously in a lower alkanol, for example in methanolic solution, if necessary under increased pressure and/or with warming, for example under about 1 to 10 bar and at 20° to 60° C.

The solvolytic liberation of hydroxyl from etherified or esterified hydroxyl groups other than those mentioned, such as from silyloxy, lower alkanoyloxy or lower alkoxycarbonyloxy, is carried out, for example, by hydrolysis (reaction with water), alcoholysis (reaction with an alcohol) or ammonolysis or aminolysis (reaction with ammonia or an amine which contains at least one free hydrogen), if necessary in the presence of an acid or basic agent and/or with warming, for example at about 20° to 100° C. Suitable acid agents are, for example, mineral acids, such as hydrogen halide acids, for example hydrochloric acid, or oxygen acids of sulfur or phosphorus, for example sulfuric or phosphoric acid, or organic sulfonic or carboxylic acids, such as lower alkanesulfonic acids or substituted or unsubstituted benzenesulfonic acids or lower alkanoic acids, for example p-toluenesulfonic acid or acetic acid. Basic hydrolysing agents are, for example, hydroxides or carbonates of alkali metals, for example potassium carbonate, sodium hydroxide or potassium hydroxide, and for alcoholysis, furthermore, corresponding alcoholates, such as alkali metal lower alkanolates, for example sodium methanolate.

Starting substances I' can be obtained, for example, by reacting compounds of the formulae

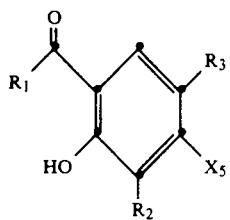

(VII)

and

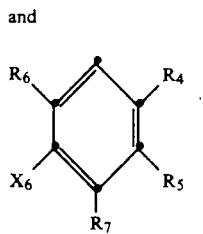

(VIII)

in which one of the radicals $X_5$ and $X_6$ is hydroxyl in the free form or in salt form and the other is a radical —O—alk'—X, i.e. a radical —O—alk—X substituted by oxo or etherified or esterified hydroxyl, such as an oxoalkylene, oxo(oxa)alkylene, oxo(dioxa)alkylene or etherified or esterified hydroxy(oxa)alkylene or hydroxy(dioxa)alkylene radical substituted by X, for example of the formula

 (Ib$^{III}$) or

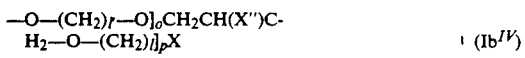 (Ib$^{IV}$)

in which X is reactive esterified hydroxyl, for example halogen, with one another.

A compound of the general formula I obtainable according to the invention can be converted into another compound of the general formula I in a manner which is known per se.

Thus, for example, a free carboxyl group $R_6$, $R_7$ and/or $R_8$ can be converted in the customary manner, for example by treatment with a diazo-lower alkane or tri-lower alkyloxonium, tri-lower alkylcarboxonium or di-lower alkylcarbonium salt, such as a hexachloroantimonate or hexafluorophosphate, or, in particular, by reaction with the corresponding alcohol or a reactive derivative, such as a carboxylic, phosphorous, sulfurous or carbonic acid ester thereof, for example a lower alkanol, N,N-di-lower alkylamino-lower alkanol, N,N-lower alkyleneamino-lower alkanol, substituted or unsubstituted N,N-(aza)-lower alkyleneamino-lower alkanol, N,N-(oxa)-lower alkyleneamino-lower alkanol or N,N-(thia)-lower alkyleneamino-lower alkanol or with a lower alkanecarboxylic acid ester, tri-lower alkyl phosphite or di-lower alkyl sulfite, to give compounds of the general formula I in which $R_6$, $R_7$ and/or $R_8$ is esterified carboxyl. The reaction with the corresponding alcohol itself can advantageously be carried out in the presence of an acid catalyst, such as a proton acid, for example hydrochloric or hydrobromic, sulfuric, phosphoric, boric, benzenesulfonic and/or toluenesulfonic acid, in an inert solvent, in particular an excess of the alcohol employed, and if necessary in the presence of a water-binding agent and/or with distillative, for example azeotropic, removal of the water of reaction and/or at elevated temperature. The reaction with a reactive derivative of the corresponding alcohol can be carried out in the customary manner, starting from a carboxylic, phosphorous, sulfurous or carbonic acid ester, for example in the presence of an acid catalyst, such as one of those mentioned above, in an inert solvent, for example in toluene, or an excess of the alcohol derivative employed or of the corresponding alcohol, if necessary with removal of the water of reaction by distillation, for example azeotropic removal by distillation. Starting from a mineral acid ester or sulfonic acid ester, the acid to be esterified is advantageously employed in the form of a salt, for example the sodium or potassium salt, and the reaction is carried out, if necessary, in the presence of a basic condensing agent, such as an inorganic base, for example sodium hydroxide or carbonate, potassium hydroxide or carbonate or calcium hydroxide or carbonate, or a tertiary organic nitrogen base, for example triethylamine or pyridine, and/or in an inert solvent, such as one of the above tertiary nitrogen bases or a polar solvent, for example in dimethylformamide, and/or at elevated temperature. The reaction with an olefine can be carried out, for example, in the presence of an acid catalyst, for example a Lewis acid, for example boron trifluoride, a sulfonic acid, for example p-toluenesulfonic acid, or, in particular, a basic catalyst, for example sodium hydroxide or potassium hydroxide, advantageously in an inert solvent, such L as an ether, for example in diethyl ether or tetrahydrofuran A free carboxyl group $R_6$, $R_7$ and/or $R_8$ can furthermore be converted into an amidated carboxyl group by reaction with ammonia or an amine containing at least one hydrogen atom in the customary manner, with dehydration of the ammonium salt intermediately formed, for example by azeotropic distillation with benzene or toluene or dry heating.

The above conversions of carboxyl into esterified or amidated carboxyl groups can, however, also be carried out by first converting a compound of the formula I in which $R_6$, $R_7$ and/or $R_8$ is carboxyl into a reactive derivative in the customary manner, for example into an acid halide by means of a halide of phosphorus or sulfur, for example by means of phosphorus trichloride or -bromide, phosphorus pentachloride or thionyl chloride, or into a reactive ester, i.e. esters with electron-attracting structures, such as the ester with phenol, thiophenol, p-nitrophenol or cyanomethyl alcohol, or a reactive amide, for example the amide derived from imidazole or 3,5-dimethylpyrazole, by reaction with a corresponding alcohol or amine, and then reacting the resulting reactive derivative with a corresponding alcohol, ammonia or the corresponding amine containing at least one hydrogen atom in the customary manner, for example as described below for the transesterification, transamidation or reciprocal conversion of esterified and amidated carboxyl groups, to give the desired group $R_4$, $R_6$ and/or $R_8$.

An esterified carboxyl group $R_6$, $R_7$ and/or $R_8$ and cyano $R_6$ and/or $R_7$ can be hydrolysed in the customary manner, for example by hydrolysis in the presence of a catalyst, for example a basic or acid agent, such as a strong base, for example sodium hydroxide or potassium hydroxide, or a mineral acid, for example hydrochloric acid, sulfuric acid or phosphoric acid, to give the free carboxyl group, cyano $R_6$ and/or $R_7$ and furthermore carbamyl. Esterified carboxyl $R_6$, $R_7$ and/or $R_8$ can likewise be converted into an amidated carboxyl group, for example by reaction with ammonia or the corresponding amine containing at least one hydrogen atom.

An esterified carboxyl group $R_6$, $R_7$ and/or $R_8$ can furthermore be transesterified in the customary manner, for example by reaction with a metal salt, such as the sodium or potassium salt, of a corresponding alcohol or with the alcohol itself in the presence of a catalyst, for example a strong base, for example sodium hydroxide or potassium hydroxide, or a strong acid, such as a mineral acid, for example hydrochloric acid, sulfuric acid or phosphoric acid, or an organic sulfonic acid, for example p-toluenesulfonic acid, or a Lewis acid, for example boron trifluoride-etherate, to give another esterified carboxyl group.

An amidated carboxyl group $R_6$, $R_7$ and/or $R_8$ can be converted into the free carboxyl group in the customary manner, for example by hydrolysis in the presence of a catalyst, for example a strong base, such as an alkali metal hydroxide or carbonate or alkaline earth metal hydroxide or carbonate, for example sodium hydroxide or carbonate or potassium hydroxide or carbonate, or a strong acid, such as a mineral acid, for example hydrochloric acid, sulfuric acid or phosphoric acid.

Substituents can furthermore be introduced into one or both phenyl rings in a compound obtainable according to the invention and/or existing substituents can be converted into other substituents. Thus, lower alkyl can be introduced by reaction with a lower alkyl halide or lower alkene or a lower alkanoic acid halide or anhydride, in each case in the presence of a Lewis acid, such as aluminium trichloride. Halogen can furthermore be introduced, for example by treatment with a halogen in the presence of a Lewis acid, such as iron-III chloride, or by reaction with N-chlorosuccinimide. Moreover, halogen, in particular iodine, can be replaced by trifluoromethyl by reaction with trifluoroiodomethane in the presence of copper.

As mentioned, depending on the choice of the starting substances and procedures, the novel compounds can be in the form of one of the possible isomers or as mixtures thereof, for example, depending on the number of asymmetric carbon atoms, as pure optical isomers, such as antipodes, or as isomer mixtures, such as racemates, diastereoisomer mixtures or racemate mixtures.

Resulting diastereomer mixtures and racemate mixtures can be resolved into the pure isomers, diastereomers or racemates by means of the physico-chemical differences of their constituents in a known manner, for example by chromatography and/or fractional crystallisation.

Resulting racemates can furthermore be resolved into the optical antipodes by known methods, for example by recrystallisation from an optically active solvent, with the aid of microorganisms, or by reaction of an acid end product with an optically active base which forms salts with the racemic acid and separation of the salts obtained in this manner, for example by means of their different solubilities, into the diastereomers, from which the antipodes can be liberated by the action of suitable agents. The more active of the two antipodes is advantageously isolated.

Resulting free compounds of the formula I, for example those in which $R_6$ and/or $R_7$ is carboxyl and/or $R_8$ is carboxyl or 5-tetrazolyl, can be converted into salts in a manner which is known per se, for example by treatment with a base or with a suitable salt of a carboxylic acid, usually in the presence of a solvent or diluent.

Resulting salts can be converted into the free compounds or resulting free compounds in which $R_8$ is capable of forming acid addition salts can be converted into acid addition salts thereof in a manner which is known per se, for example by treatment with an acid reagent, such as a mineral acid, or one of the salt-forming acids mentioned.

The compounds, including their salts, can also be obtained in the form of their hydrates or can include the solvent used for the crystallisation.

As a result of the close relationship between the novel compounds in the free form and in the form of their salts, the free compounds or their salts, where appropriate, are correspondingly and appropriately also to be understood as the corresponding salts or, respectively, free compounds above and below.

The invention also relates to those embodiments of the process in which a compound obtainable as an intermediate at any stage of the process is used as the starting substance and the missing steps are carried out, or a starting substance is used in the form of, or, in particular, forms under the reaction conditions, a salt and/or racemate or antipode.

The invention likewise relates to the novel starting substances and intermediates arising in the processes according to the invention and their preliminary stages and to processes for their preparation.

Preferably, starting substances are used and the reaction conditions are chosen such that the compounds mentioned above as particularly preferred are obtained.

In this connection, particular reference is made to compounds of the formulae VII, in which $X_5$ is hydroxyl, and XII and their salts, which have been developed specifically as starting substances for compounds of the formula I.

The invention accordingly likewise relates to compounds of the formula

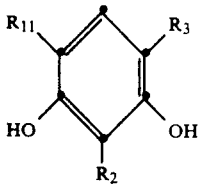

(XXXIII)

in which $R_2$ is fluorinated lower alkyl, $R_3$ is hydrogen, lower alkoxy, trifluoromethyl or halogen and $R_{11}$ is hydrogen or a group of the formula $R_1$—C(=O)—, in which $R_1$ is lower alkyl, and their salts, a process for their preparation and their use as intermediates, for example for the preparation of medicament active ingredients.

$R_1$, $R_2$ and $R_3$ have here, for example, the meanings given for compounds I. Salts of compounds XXXIII are likewise preferably metal salts of the type mentioned for compounds I.

The invention relates, for example, to compounds of the formulae VII in which $X_5$ is hydroxyl, and/or compounds of the formula XII, and in each case their salts, processes for their preparation and their use.

The invention particularly relates to compounds of the formulae VII, XII and XXXIII in which $R_1$ is lower alkyl having not more than 4 C atoms, such as methyl, $R_2$ is ω-fluoro-, ω,ω-difluoro- or ω,ω,ω-trifluoro-lower alkyl having not more than 4, for example 1 or 3, C atoms, such as trifluoromethyl or 3,3,3-trifluoropropyl, and $R_3$ is hydrogen, and their salts, processes for their preparation and their use.

The invention preferably relates to compounds of the formulae VII, XII and XXXIII in which $R_1$ is lower alkyl having not more than 4 C atoms, such as methyl, $R_2$ is ω,ω,ω-trifluoro-lower alkyl having not more than 4, for example 1 or 3, C atoms, such as 3,3,3-trifluoropropyl, and $R_3$ is hydrogen, and their salts, processes for their preparation and their use.

The invention relates, in particular, to 2-(3,3,3-trifluoropropyl)-resorcinol of the formula XII and 4-acetyl-2-(3,3,3-trifluoropropyl)-resorcinol of the formula VII in the free form or in salt form, processes for the preparation thereof and the use thereof.

The invention furthermore relates to a process for the preparation of compounds of the formula XXXIII and their salts. This comprises
i) in a compound of the formula

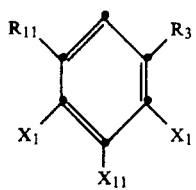

(XXIV)

in which at least one of the radicals $X_1$ is etherified hydroxyl R and a radical $X_1$ which differs from this is free hydroxyl and $X_{11}$ is a group which can be replaced by the desired radical $R_2$ or converted into this radical, replacing $X_{11}$ by the desired radical or converting it into this radical, splitting etherified hydroxyl R to give hydroxyl and, if desired, converting the compound obtainable according to the process into another compound of the formula XXXIII, in particular introducing a group of the formula $R_1$—C(=O)— instead of hydrogen $R_{11}$ and/or converting a free compound obtainable according to the process into a salt or a salt obtainable according to the process into the free compound Groups $X_{11}$ which can be replaced by radicals $R_2$ are, for example, halogen atoms —Hal with an atomic number of 19 to not more than 53, i.e. chlorine, bromine or iodine, in particular bromine or iodine, or metallic radicals, for example a group of the formula —$M^I$, —$M^{II}/2$ or —$M^{II}$—Hal, in which $M^I$ is an alkali metal atom, for example lithium or sodium, or monovalent copper, $M^{II}$ is an alkaline earth metal atom, for example magnesium, zinc or cadmium, or divalent copper, and —Hal is halogen with an atomic number of 19 to not more than 53.

Replacement of the groups $X_{11}$ mentioned by radicals $R_2$ is carried out in the customary manner, for example by reaction with a compound of the formula $X_{10}$—$R_2$ (XV), in which one of the radicals $X_{10}$ and $X_{11}$ is a metallic radical and the other is halogen, or by reaction with a compound of the formula $X_{10}$—$R_2$ (XV), in which both radicals $X_{10}$ and $X_{11}$ are a halogen —Hal, in the presence of a metal, preferably one of those mentioned, in particular copper powder. The reaction of compounds XXXIV and XV in which $X_{10}$ or $X_{11}$ is a metallic radical is preferably carried out in the presence of an aliphatic or cycloaliphatic ether, such as a di-lower alkyl ether, for example diethyl ether or tertiary butoxymethane, or a 5-membered to 7-membered oxa- or dioxacycloalkene, for example tetrahydrofuran or 1,4-dioxane, if necessary in the presence of a solvent or diluent, for example dimethylformamide, advantageously under an inert gas, such as argon. The reaction of compounds XXXIV and XV in which $X_{10}$ and $X_{11}$ are both halogen Hal in the presence of a metal is preferably carried out with heating, for example to about 80° to 150° C., in an inert, high-boiling solvent, such as dimethylformamide, 1,2-dimethoxyethane, 1,5-dimethoxy-(3-oxa)butane or diphenyl ether, advantageously likewise under an inert gas, such as argon.

Starting substances XV or XXXIV in which $X_{10}$ or $X_{11}$ is a metallic radical are preferably formed in situ by treatment of the corresponding compound XV or XXXIV in which $X_{10}$ or $X_{11}$ is a halogen Hal with the corresponding metal, and are employed without being isolated.

Starting from compounds XXXIV in which $R_3$ is likewise a halogen Hal, the replacement reactions mentioned are interfered with by side reactions. These can be by-passed by using a corresponding nitro compound as the starting substance and subsequently reducing the nitro group to the amino group in the customary manner, for example with iron and hydrochloric acid, and replacing this by the desired halogen atom, for example by means of sodium nitrite in a hydrogen halide acid H—Hal. Condensation of compounds XV and XXXIV in which $X_{10}$ or $X_{11}$ is a metallic radical is furthermore not particularly suitable for the preparation of compounds XXXIII in which $R_{11}$ is an acyl group $R_1$—C(=O)—.

In a preferred embodiment, for example, compounds of the formula XXXIII in which $R_{11}$ is hydrogen and $R_2$ is trifluoromethyl are obtained by heating a compound XXXIV in which $X_{11}$ is bromine or iodine, $X_1$ is etherified hydroxyl R and $R_{11}$ is hydrogen, at about 120°-180° C. with trifluoromethyl iodide and copper powder in dimethylformamide and subsequently converting etherified hydroxyl R into hydroxyl.

Groups $X_{11}$ which can be converted into radicals $R_2$ are, for example, fluorinated lower alkenyl radicals, such as 3-fluoro-, 3,3-difluoro- or 3,3,3-trifluoroprop-1-enyl or 3-fluoro- or 3,3-difluoroprop-2-enyl, fluorinated lower alkynyl radicals, such as 3-fluoro-, 3,3-difluoro- or 3,3,3-trifluoroprop-1-ynyl, and furthermore fluorinated hydroxy-lower alkyl radicals, such as 3-fluoro-, 3,3-difluoro- or 3,3,3-trifluoro-1-hydroxy-propyl.

Conversion of the groups $X_{11}$ mentioned into radicals $R_2$ is carried out, for example, by reduction. Reducing agents are, for example, hydrogen in the presence of a hydrogenation catalyst, such as a platinum, palladium or rhodium catalyst, for example platinum oxide. Treatment with catalytically activated hydrogen (hydrogenation) is carried out under normal or at most moderately increased pressure and/or temperature conditions, for example under an increased pressure of about 0 to 5 bar and/or in the temperature range from about 20° to about 80° C.

Starting substances XXXIV in which $X_{11}$ is a fluorinated lower alk-1-enyl or 1-hydroxy-lower alkyl radical, $R_{11}$ is hydrogen, the radicals $X_1$ are etherified hydroxyl groups R and $R_3$ is other than halogen Hal are obtained, for example, by treating a corresponding compound XXXIV in which $X_{11}$ is a halogen Hal with a metal $M^I$ or $M^{II}$, reacting the resulting compound XXXIV in which $X_{11}$ is a group $-M^I$, $-M^{II}/2$ or $-$MHal with a fluorinated oxo-lower alkane and, for the preparation of compounds XXXIV in which $X_{11}$ is a fluorinated lower alk-1-enyl radical, detaching water from the fluorinated 1-hydroxyalkyl compound primarily obtained, for example by acetylation and subsequent acid treatment.

Starting substances XXXIV in which $X_{11}$ is a mono- or difluorinated lower alk-2-enyl radical and at least one of the radicals $X_1$ is free hydroxyl are obtained, for example, by subjecting a compound of the formula

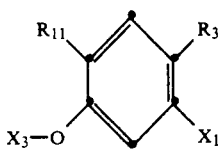
(XXXV)

to allyl rearrangement, for example by heating to about 150° to 250° C., preferably to about 190° to 220° C., advantageously in a solvent, such as diphenyl ether or N,N-dimethyl- or N,N-diethylaniline. The radical $X_3$ is also thereby rearranged, so that the corresponding 3-fluoro- or 3,3-difluoro-lower alk-2-enyl radical is formed from a 1-fluoro- or 1,1-difluoro-lower alk-2-enyl radical.

Compounds XXXIV in which $X_{11}$ is a fluorinated lower alk-1-ynyl radical and $R_{11}$ is hydrogen are obtained, for example, by adding halogen onto $X_{11}$ in a corresponding compound XXXIV in which $X_{11}$ is a fluorinated lower alkenyl radical with at least 2 hydrogen atoms on the C atoms of the double bond, and detaching 2 moles of hydrogen halide in the customary manner.

Compounds of the formula XXXIII in which $R_2$ is 3,3,3-trifluoropropyl and $R_3$ and $R_{11}$ are as defined, and their salts, are obtained in a particularly easy manner according to a procedure which is novel overall and/or in important individual steps, by reacting a compound of the formula

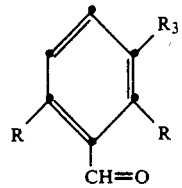
(XX)

in which R is etherified hydroxyl, such as lower alkoxy, for example methoxy, with an etherate of 1,1-dichloro-2,2,2-trifluoro-ethyl-zinc chloride, for example of the formula $CF_3CCl_2ZnCl(C_2H_5)_2O$ (XXI) in an inert solvent, for example in dimethylformamide, to give the corresponding compound of the formula

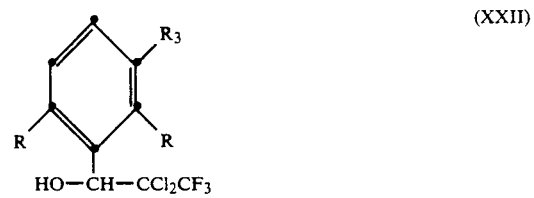
(XXII)

acylating this in the side chain, for example acetylating, for example by means of acetic anhydride in pyridine, converting the reaction product of the formula

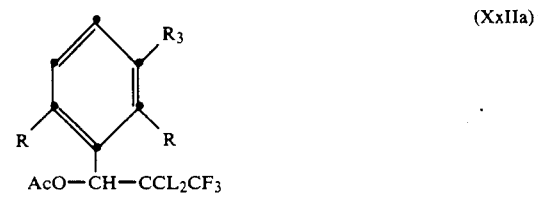
(XXIIa)

in which the radical Ac is the acyl group introduced, for example acetyl, into the corresponding compound of the formula

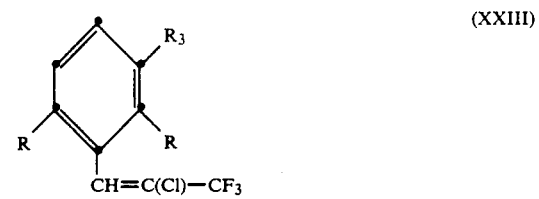
(XXIII)

with a metallic reducing agent, for example a base metal, preferably with activated zinc dust in the presence of ammonium chloride, detaching hydrogen chloride from this product by treatment with a metal base, such as an alkali metal or alkaline earth metal alcoholate, for example with potassium tertiary butanolate, hydrogenating the side chain in the resulting compound of the formula

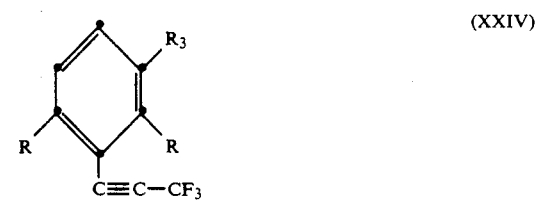
(XXIV)

for example in the presence of palladium-on-charcoal, and splitting the etherified hydroxyl groups R to give hydroxyl, for example by treatment with hydrobromic acid in methylene chloride, if desired introducing a radical $R_{11}$ of the formula $R_1-C(=O)-$ and if desired converting a resulting free compound into a salt or a resulting salt into the free compound.

The introduction of a radical $R_{11}$ of the formula $R_1-C(=O)-$ which can subsequently be carried out, if appropriate, is effected, for example, as described under process variant a) or b), for example by reaction with a compound of the formula $R_1-X_2$ (IV), in which $X_2$ is free or functionally modified carboxyl, such as carboxyl, halogenocarbonyl of the formula $-C(=O)-Hal$ or carboxyl converted into an anhydride, for example of the formula $-C(=O)-O-C(=O)-R_1$, in the presence of a Lewis acid—as defined under process variant b)—for example by reaction with an acid of the formula (IV; $X_2=$carboxyl) in the presence of zinc chloride. Reciprocal conversion of resulting acids and salts is likewise carried out as described for compounds of the formula I.

The present invention also relates to pharmaceutical products which contain one of the compounds of the formula I according to the invention or a pharmaceutically acceptable salt thereof. The pharmaceutical products according to the invention are those which are intended for topical and local as well as enteral, such as oral or rectal, and parenteral administration to and for inhalation by warm-blooded organisms and contain the pharmacological active ingredient by itself or together with a pharmaceutically acceptable carrier. The dosage of the active ingredient depends on the species of warm-blooded organism, the age and individual condition and the mode of administration.

The novel pharmaceutical products contain, for example, from about 10% to about 95%, preferably from about 20% to about 90%, of the active ingredient. Pharmaceutical products according to the invention are, for example, those in aerosol or spray form or in dosage unit forms, such as sugar-coated tablets, tablets, capsules or suppositories, and furthermore ampoules.

The pharmaceutical products of the present invention are prepared in a manner which is known per se, for example by means of conventional mixing, granulation, coating, dissolving or lyophilising processes. Thus, pharmaceutical products for oral use can be obtained by combining the active ingredient with solid carriers, a resulting mixture can be granulated, if appropriate, and the mixture or granules, if desired or necessary, can be processed to tablets or sugar-coated tablet cores, after addition of suitable adjuncts.

Suitable carriers are, in particular, fillers, such as sugar, for example lactose, sucrose, mannitol or sorbitol, cellulose products and/or calcium phosphates, for example tricalcium phosphate or calcium hydrogen phosphate, and also binders, such as starch pastes, for example maize, wheat, rice or potato starch paste, gelatine, tragacanth, methylcellulose and/or polyvinylpyrrolidone, and/or, if desired, disintegrators, such as the abovementioned starches, and furthermore carboxymethyl starch, crosslinked polyvinylpyrrolidone, agar and alginic acid or a salt thereof, such as sodium alginate. Adjuncts are, in particular, glidants and lubricants, for example silicic acid, talc, stearic acid or salts thereof, such as magnesium stearate or calcium stearate, and/or polyethylene glycol. Sugar-coated tablet cores are provided with suitable coatings, which may be resistant to gastric juice, using, inter alia, concentrated sugar solutions, which contain, if appropriate, gum arabic, talc, polyvinylpyrrolidones, polyethylene glycol and/or titanium dioxide, shellac solutions in suitable organic solvents or solvent mixtures or, for the preparation of coatings which are resistant to gastric juice, solutions of suitable cellulose products, such as acetylcellulose phthalate or hydroxypropylmethylcellulose phthalate. Dyes or pigments may be added to the tablets or coatings of sugar-coated tablets, for example to identify or indicate different doses of active ingredient.

Further pharmaceutical products for oral use are dry-filled capsules of gelatine, and also soft, sealed capsules made of gelatine and a plasticiser, such as glycerol or sorbitol. The dry-filled capsules can contain the active ingredient in the form of granules, for example mixed with fillers, such as lactose, binders, such as starches, and/or lubricants, such as talc or magnesium stearate, and, if appropriate, stabilisers. In soft capsules, the active ingredient is preferably dissolved or suspended in suitable liquids, such as fatty oils, paraffin oil or liquid polyethylene glycols, to which stabilisers can likewise be added.

Pharmaceutical products for rectal administration are, for example, suppositories, which consist of a combination of the active ingredient and a suppository base. Suitable suppository bases are, for example, natural or synthetic triglycerides, paraffin hydrocarbons, polyethylene glycols or higher alkanols. Rectal gelatine capsules containing a combination of the active ingredient with a base can furthermore also be used; base substances are, for example, liquid triglycerides, polyethylene glycols or paraffin hydrocarbons.

Aqueous solutions of an active ingredient in water-soluble form, for example of a water-soluble salt, and furthermore suspensions of the active ingredient, such as corresponding oily injection suspensions, using suitable lipophilic solvents or vehicles, such as fatty oils, for example sesame oil, or synthetic fatty acid esters, for example ethyl oleate or triglycerides, or aqueous injection suspensions containing viscosity-increasing substances, for example sodium carboxymethylcellulose, sorbitol and/or dextran and, if appropriate, also stabilisers, are chiefly suitable for parenteral administration.

Inhalation products for treatment of the respiratory tract by nasal or bucal administration are, for example, aerosols or sprays which can disperse the pharmacological active ingredient in the form of a powder or in the form of drops of a solution or suspension. Products with powder-dispersing properties usually contain, in addition to the active ingredient, a liquid propellant with a boiling point below room temperature and, if desired, adjuncts, such as liquid or solid non-ionic or anionic surfactants and/or diluents. Products in which the pharmacological active ingredient is in solution contain, in addition to this, a suitable propellant, and furthermore, if necessary, an additional solvent and/or a stabiliser. Instead of the propellant, compressed air can also be used, it being possible for this to be produced as required by means of a suitable compression and expansion device.

Pharmaceutical products for topical and local use are, for example, for the treatment of skin, lotions and creams containing a liquid or semi-solid oil-in-water or water-in-oil emulsion, and ointments (these preferably containing a preservative), and, for the treatment of eyes, eye drops containing the active compound in aqueous or oily solution and eye ointments, which are preferably prepared in sterile form, and, for the treatment of the nose, powders, aerosols and sprays (similar to those described above for the treatment of the respiratory tract) and coarse powders which are administered by rapid inhalation through the nostrils, and nose drops containing the active compound in aqueous or oily solution, or, for local treatment of the mouth, sweets for sucking, containing the active compound in a mass generally formed from sugar and gum arabic or tragacanth, to which flavouring agents may be added, and pastilles containing the active substance in an inert mass, for example of gelatine and glycerol or sugar and gum arabic.

The invention also relates to the use of the novel compounds of the formula I and of their salts as pharmacologically active compounds, for example as antiallergics or, in particular, antiinflammatories, preferably in the form of pharmaceutical products. The daily dose administered to a warm-blooded organism weighing about 70 kg is from about 200 mg to about 1,200 mg.

The following examples illustrate the invention described above without in any way restricting the scope thereof. Temperatures are given in degrees Celsius.

EXAMPLE 1

A solution of 3 g (4.5 mmol) of N{{3-{3[- 4-acetyl-3-hydroxy-2-(3,3,3-trifluoropropyl)-phenoxy}-propoxy}-4-chloro-6-methyl-phenyl}}-1-(4-methoxybenzyl)-tetrazole-5-carboxamide in 90 ml of trifluoroacetic acid and 9 ml of anisole is refluxed for 60 minutes. The reaction mixture is concentrated under reduced pressure, about 150 ml of ether and 300 ml of petroleum ether are added and the crystals are filtered off. The N-{{3-{3-[4-acetyl-3-hydroxy-2-(3,3,3-trifluoropropyl)-phenoxy]-propoxy}-4-chloro-6-methyl-phenyl}}-1H-tetrazole-5-carboxamide thus obtained, of melting point 236°–238° (decomposition) is dissolved in 50 ml of tetrahydrofuran, and one equivalent of sodium, dissolved in 5 ml of methanol, is added. After addition of ether, crystallisation starts. The sodium salt of N-{{3-{3-[4-acetyl-3-hydroxy-2-(3,3,3-trifluoropropyl)-phenoxy]-propoxy}-4-chloro-6-methylphenyl}}-1H-tetrazole-5-carboxamide of melting point 9020 (decomposition) is thus obtained.

N-{{3-{3-[4-Acetyl-3-hydroxy-2-(3,3,3-trifluoropropyl)-phenoxy]-propoxy}-4-bromo-6-methyl-phenyl}}-1H-tetrazole-5-carboxamide of melting point 245°–248° (decomposition) is obtained in an analogous manner by refluxing N-{{3-{3-[4-acetyl-3-hydroxy-2-(3,3,3-trifluoropropyl)-phenoxy]-propoxy}-4-bromo-6-methylphenyl}}-1-(4-methoxybenzyl)-tetrazole-5-carboxamide in trifluoroacetic acid/anisole. The sodium salt of N-{{3-{3-[4-acetyl-3-hydroxy-2-(3,3,3-trifluoropropyl)-phenoxy]-propoxy}-4-bromo-6-methyl-phenyl}}-1H-tetrazole-5-carboxamide (melting point 120°–130° C.) is analogously obtained by dissolving the free compound in tetrahydrofuran and reacting it with one equivalent of sodium dissolved in 5 ml of methanol.

The starting material can be prepared, for example, as follows:

Stage A: 1,1-Dichloro-2,2,2-trifluoro-ethyl-zinc chloride diethyl etherate, $CF_3CCl_2ZnCl(C_2H_5)O$ 65.4 g (1 mole) of zinc dust (activated according to Fieser & Fieser) are suspended in 800 ml of diethyl ether in a 1 l three-necked round-bottomed flask and 188 g (1 mole) of $CF_3CCl_3$ are slowly added under a blanket of argon. The mixture is subsequently stirred at room temperature for 20 hours. The reaction mixture is then filtered over "Selecta" filter flocculant material, the complex precipitating in crystalline form after cooling the filtrate or after it has cooled down. The complex is recrystallised from diethyl ether, for further purification. The excess diethyl ether is decanted off and the colourless crystalline residue is dried in vacuo. 1,1-Dichloro-2,2,2-trifluoro-ethyl-zinc chloride diethyl etherate of melting point 105° is obtained, yield 80%.

Stage B:
1,3-Dimethoxy-2-(1-hydroxy-2,2-dichloro-3,3,3-trifluoropropyl)-benzene 130.1 g (0.40 mole) of 1,1-dichloro-2,2,2-trifluoroethyl-zinc chloride diethyl etherate in 700 ml of absolute dimethylformamide are introduced into a three-necked round-bottomed flask (1,000 ml) with a thermometer, bubble counter and argon connection, after evacuating/flushing with argon 3 times. 51.0 g (0.32 mole) of 2,6-dimethoxybenzaldehyde are then added all at once. The yellow clear reaction solution is stirred at room temperature for 72 hours and then poured onto a mixture of 600 g of ice and 600 ml of 10% hydrochloric acid. After extraction with ether, washing with 2% hydrochloric acid and brine, drying over magnesium sulfate and concentration, a dark red oil is obtained, from which red-brown crystals of 1,3-dimethoxy-2-(1-hydroxy-2,2-dichloro-3,3,3-trifluoro-propyl)-benzene precipitate, yield 99%. This does not have to be subsequently purified for further processing.

Stage C:
1,3-Dimethoxy-2-(1-acetoxy-2,2-dichloro-3,3,3-trifluoropropyl)-benzene 31 ml (0.33 mole) of acetic anhydride are added to 97.6 g (0.30 mole) of 1,3-dimethoxy-2-(1-hydroxy-2,2-dichloro-3,3,3-trifluoro-propyl)-benzene in a 500 ml pear-shaped flask at room temperature. 30 ml (0.36 mole) of pyridine are then added to the dark red solution (weakly exothermic). The reaction solution is stirred at room temperature for 3 days. The reaction mixture is then poured onto ice and acidified with 10% hydrochloric acid. It is extracted with ether and the extract is washed with water and brine, dried over magnesium sulfate and evaporated to dryness. The 1,3-dimethoxy-2-(1-acetoxy-2,2-dichloro-3,3,3-trifluoropropyl)-benzene which remains (yield 87%) is employed for stage D without further purification.

Stage D:
1,3-Dimethoxy-2-(2-chloro-3,3,3-trifluoroprop-1-enyl)-benzene 96.5 g (0.266 mole) of 1,3-dimethoxy-2-(1-hydroxy-2,2-dichloro-3,3,3-trifluoro-propyl)-benzene are dissolved in 1,000 ml of ethanol in a 1.5 l sulfonating flask with a thermometer, condenser and bubble counter, and 30 g (0.56 mole) of ammonium chloride are added. Zinc activated according to Fieser & Fieser (36.9 g=0.564 mole) is added in portions to the resulting brownish suspension, the reaction temperature rising to 42°. Stirring is continued overnight and the grey-yellow reaction mixture is then poured onto ice-water and extracted with ether and the extract is washed with water (3×) and brine, dried over magnesium sulfate and evaporated. 1,3-Dimethoxy-2-(2-chloro-3,3,3-trifluoroprop-1-enyl)-benzene (yield: 94%) is obtained as a reddish oil.

Zinc dust is activated as follows: suspension in 5% HCl and decanting (exothermic) twice, suspension in H₂O and decanting 3 times, suspension in methanol and decanting twice, suspension with ether and decanting 3 times; drying under greatly reduced pressure and storage under argon.

Stage E:
1,3-Dimethoxy-2-(3,3,3-trifluoroprop-1-ynyl)-benzene 30.7 g of potassium tertiary butanolate in 900 ml of tertiary butanol are introduced into a 1.5 l sulfonating flask with a thermometer, condenser, bubble counter and dropping funnel. 63.7 g (0.25 mole) of 1,3-dimethoxy-2-(2-chloro-3,3,3-trifluoroprop-1-enyl)-benzene in 100 ml of tertiary butanol are added dropwise to this clear, colourless solution (weakly exothermic) and the reaction is brought to completion by stirring at room temperature for 24 hours. The orange suspension is poured onto ice and extracted with ether and the extract is washed with water, N bicarbonate solution and brine, dried over magnesium sulfate and concentrated until crystals precipitate. The crystal mass is cooled, filtered cold and washed with a little ice-cold petroleum ether. 1,3-Dimethoxy-2-(3,3,3-trifluoroprop-1-ynyl)-benzene is obtained in the form of pale beige, fine crystals of melting point 110°–111° (yield 73%).

Stage F:
1,3-Dimethoxy-2-(3,3,3-trifluoropropyl)-benzene 41.5 g (0.18 mole) of 1,3-dimethoxy-2-(3,3,3-trifluoroprop-1-ynyl)-benzene are dissolved in tetrahydrofuran and hydrogenated in the presence of palladium-on-charcoal at room temperature under normal pressure. The catalyst is filtered off over diatomaceous earth and washed with tetrahydrofuran and the filtrate is concentrated. Drying under reduced pressure gives crystalline 1,3-dimethoxy-2-(3,3,3-trifluoropropyl)-benzene (yield 87%).

Stage G: 2-(3,3,3-Trifluoropropyl)-resorcinol 30.5 g (0.13 mole) of 1,3-dimethoxy-2-(3,3,3-trifluoropropyl)-benzene in 275 ml of methylene chloride are introduced into a 1.5 l sulfonating flask with a thermometer, bubble counter, dropping funnel with cooling jacket and argon connection and cooled to −75°. 340 ml of a precooled 1 molar solution of boron tribromide in methylene chloride are now added dropwise such that the reaction temperature does not rise above −70° (about 90 minutes). After subsequently stirring at room temperature for 6 hours, the red reaction solution is poured onto 800 ml of ice-water. The organic base is separated off, the aqueous phase is extracted again with ether and the combined organic phases are washed with brine, dried over magnesium sulfate and evaporated. 2-(3,3,3-Trifluoropropyl)-resorcinol is obtained in the form of red crystals of melting point 82°–84° (yield 100%).

Stage H:
2,4-Dihydroxy-3-(3,3,3-trifluoropropyl)-acetophénone 21.0 g (0.154 mole) of zinc chloride in 27 ml of glacial acetic acid are introduced into a 100 ml three-necked round-bottomed flask with a condenser, bubble counter and thermometer and heated to 120°, a clear, colourless solution forming. 27.0 g (0.13 mole) of 2-(3,3,3-trifluoropropyl)-resorcinol are added at this temperature, whereupon the temperature falls to 82°. The red, clear solution is refluxed (132°) for a further 4 hours and allowed to cool. A red suspension is obtained; this is poured onto 440 ml of half-concentrated hydrochloric acid and extracted 3 times with ether. The organic phase is washed with brine, dried over magnesium sulfate and concentrated to a high degree. The reddish crystals obtained are suspended in pentane, filtered off with suction and washed with pentane 2,4-Dihydroxy-3-(3,3,3-trifluoropropyl)-acetophenone is obtained, yield: 26.5 g of yellow crystals of melting point 180°–184°; 82%

Stage I:
4-(3-Bromopropoxy)-2-hydroxy-3-(3,3,3-trifluoropropyl)-acetophenone 3.32 g of potassium carbonate and 0.5 g of potassium iodide are added to a solution of 2.45 ml of 1,3-dibromopropane in 30 ml of acetone and the mixture is refluxed. A solution of 1.98 g of 2,4-dihydroxy-3-(3,3,3-trifluoropropyl)-acetophenone in 10 ml of acetone is added dropwise in the course of 2 hours and the mixture is refluxed for a further 3 hours. The reaction mixture is filtered and the filtrate is evaporated in vacuo. The residue is dissolved in 50 ml of methylene chloride and the solution is washed with 10 ml of water. The organic phase is dried over sodium sulfate and evaporated in vacuo and the residue is chromatographed on 100 g of silica gel with methylene chloride as the mobile phase. 4-(3-Bromopropoxy)-2-hydroxy-3-(3,3,3-trifluoropropyl)-acetophenone is eluted in the first fraction, and, after evaporation, is obtained in the form of colourless crystals of melting point 70°–72° C.

Stage J:
3-{3-[4-Acetyl-3-hydroxy-2-(3,3,3-trifluoropropyl)-phenoxy]-propoxy}-4-chloro- or -bromo-6-methyl-nitrobenzene A spatula-tip of potassium iodide and 3.5 g (9.5 mmol) of 4-(3-bromopropoxy)-2-hydroxy-3-(3,3,3-trifluoropropyl)-acetophenone are added to a suspension of 1.87 g (10 mmol) of 2-chloro-4-methyl-5-nitrophenol and 1.5 g (10.5 mmol) of calcined potassium carbonate in 30 ml of ethyl methyl ketone and the mixture is refluxed for 10 hours. The reaction mixture is cooled, poured onto water and extracted three times with methylene chloride. The organic phases are combined, washed with water, dried over sodium sulfate and concentrated to dryness under reduced pressure. Crystallisation of the residue from ether/petroleum ether gives 3-{3-[4-acetyl-3-hydroxy-2-(3,3,3-trifluoropropyl)-phenoxy]-propoxy}-4-chloro-6-methyl-nitrobenzene of melting point 118°–120°.

3-{3-[4-Acetyl-3-hydroxy-2-(3,3,3-trifluoropropyl)-phenoxy]-propoxy}-4-bromo-6-methyl-nitrobenzene of melting point 106°–109° are obtained in an analogous manner starting from 2-bromo-4-methyl-5-nitrophenol.

Stage K:
3-{3-[4-Acetyl-3-hydroxy-2-(3,3,3-trifluoropropyl)-phenoxy]-propoxy}-4-chloro- or -bromo-6-methyl-aniline 1.0 g of Raney nickel is added to a solution of 3.7 g of 3-[3-(4-acetyl-3-hydroxy-2-(3,3,3-trifluoropropyl)-phenoxy)-propoxy]-4-chloro-6-methyl-nitrobenzene in 40 ml of tetrahydrofuran and the starting substance is hydrogenated at room temperature. The catalyst is filtered off and washed with tetrahydrofuran. The filtrate is evaporated to dryness under reduced pressure and the residue is crystallised from ether/petroleum ether. 3-{3-[4-Acetyl-3-hydroxy-2-(3,3,3-trifluoropropyl)-phenoxy]-propoxy}-4-chloro-6-methyl-aniline of melting point 111°–113° is thus obtained.

3-{3-[4-Acetyl-3-hydroxy-2-(3,3,3-trifluoropropyl)-phenoxy]-propoxy}-4-bromo-6-methyl-aniline of melting point 124°–126° is obtained in an analogous manner starting from 3-{3-[4-acetyl-3-hydroxy-2-(3,3,3-trifluoropropyl)-phenoxy]propoxy}-4-bromo-6-methyl-nitrobenzene.

Stage L:
N-{{3-{3-[4-Acetyl-3-hydroxy-2-(3,3,3-trifluoropropyl)-phenoxy]-propoxy}-4-chloro- or -bromo-6-methyl-phenyl}}-1-(p-methoxy-benzyl)-tetrazole-5-carboxamide 0.66 ml (7.7 mmol) of oxalyl chloride is added to a suspension of 2.07 g (7.7 mmol) of potassium[1-(4-methoxybenzyl)-tetrazole]-5-carboxylate in 30 ml of benzene and 0.5 ml of pyridine at 0°–5° and the mixture is stirred at room temperature for 30 minutes. The reaction mixture is concentrated under reduced pressure, the residue is taken up in benzene and the mixture is evaporated again under reduced pressure. The residue is suspended in 200 ml of methylene chloride and the suspension is added dropwise to a solution of 2.6 g (5.8 mmol) of 3-{3-[4-acetyl-3-hydroxy-2-(3,3,3-trifluoropropyl)-phenoxy]-propoxy}-4-chloro-6-methyl-aniline and 0.61 ml of pyridine in 30 ml of methylene chloride at 0°–5° in the course of 10 minutes. The mixture is then stirred at room temperature for 3 hours. The reaction mixture is diluted with methylene chloride and washed twice with water. The organic phase is dried over sodium sulfate and evaporated under reduced pressure. Crystallisation of the residue from ether gives N-{{3-{3-[4-acetyl-3-hydroxy-2-(3,3,3-trifluoropropyl)-phenoxy]-propoxy}-4-chloro-6-methyl-phenyl}}-1-(4-methoxybenzyl)-tetrazole-5-carboxamide of melting point 148°–150°.

N-{{3-{3-[4-Acetyl-3-hydroxy-2-(3,3,3-trifluoropropyl)-phenoxy]-propoxy}-4-bromo-6-methyl-phenyl}}-1-(4-methoxy-benzyl)-tetrazole-5-carboxamide of melting point 140°–142° C. is obtained in an analogous manner starting from 3-{3-[4-acetyl-3-hydroxy-2-(3,3,3-trifluoropropyl)-phenoxy]-propoxy}-4-bromo-6-methyl-aniline.

EXAMPLE 2

A solution of 0.36 ml (3.57 mmol) of methyl chlorooxalate in 5 ml of methylene chloride is added dropwise to a solution, cooled to 0°, of 1.75 g (3.57 mmol) of 3-{3-[4-acetyl-3-hydroxy-2-(3,3,3-trifluoropropyl)-phenoxy]-propoxy}-4-bromo-6-methyl-aniline (Example 1) and 0.55 ml (3.57 mmol) of triethylamine in 15 ml of methylene chloride in the course of 5 minutes. The reaction mixture is subsequently stirred at room temperature for 90 minutes and poured onto ice-water and the organic phase is separated off. The organic phase is washed with water, dried over sodium sulfate and concentrated under reduced pressure. Crystallisation of the residue from methylene chloride/ether gives methyl N-{{3-{3-[4-acetyl-3-hydroxy-2-(3,3,3-trifluoropropyl)-phenoxy]-propoxy{-4-bromo-6-methyl-phenyl}}-oxamate of melting point 139°–140°.

EXAMPLE 3

A suspension of 1.75 g (3 mmol) of methyl N-{{3-{3-[4-acetyl-3-hydroxy-2-(3,3,3-trifluoropropyl)-phenoxy]-propoxy}-4-bromo-6-methyl-phenyl}}-oxamate (Example 2) in 30 ml of methanol and 3.2 ml of N sodium hydroxide solution is refluxed for 60 minutes. The reaction mixture is concentrated under reduced pressure, the residue is dissolved in acetone and dilute sodium hydroxide solution and the solution is acidified with dilute hydrochloric acid. The product which has precipitated is filtered off and washed neutral with water. N-{{3-{3-[4-Acetyl-3-hydroxy-2-(3,3,3-trifluoropropyl)-phenoxy]-propoxy}-4-bromo-6-methyl-phenyl}}-oxamic acid of melting point 207°–209° is thus obtained.

EXAMPLE 4

1.55 g (2.76 mmol) of N-{{3-{3-[4-acetyl-3-hydroxy-2-(3,3,3-trifluoropropyl)-phenoxy]-propoxy}-4-bromo-6-methylphenyl}}-oxamic acid (Example 3) are dissolved hot in 300 ml of acetone, and a solution of 411 mg (2.8 mmol) of triethanolamine in 10 ml of acetone is added. The reaction solution is concentrated to 50 ml under reduced pressure. After addition of ether, crystallisation starts. The product which has precipitated out is filtered off and washed with ether. The triethanolammonium salt of N-{{3-{3-[4-acetyl-3-hydroxy-2-(3,3,3-trifluoropropyl)-phenoxy]-propoxy}-4-bromo-6-methyl-phenyl}}-oxamic acid is thus obtained; melting point 133°–135°.

EXAMPLE 5

A solution of 1.9 ml (21 mmol) of methyl chlorooxalate in 8 ml of methylene chloride is added dropwise to a solution, cooled to 0°, of 7.5 g of 3-{3-[4-acetyl-3-hydroxy-2-(3,3,3-trifluoropropyl)-phenoxy]-propoxy}-6-methylaniline and 3.0 g of triethylamine in 60 ml of methylene chloride in the course of about 5 minutes. The reaction mixture is subsequently stirred at room temperature for 90 minutes and poured onto ice-water and the organic phase is separated off. The methylene chloride phase is washed with water, dried over sodium sulfate and concentrated under reduced pressure. Crystallisation of the residue from methylene chloride/ether gives methyl N-{{3-{3-[4-acetyl-3-hydroxy-2-(3,3,3-trifluoropropyl)-phenoxy]-propoxy}-6-methylphenyl}}-oxamate.

Methyl N-{{3-{3-[4-acetyl-3-hydroxy-2-(3,3,3-trifluoropropyl)-phenoxy]-propoxy}-phenyl}}-oxamate is obtained in an analogous manner starting from 3-{3-[4-acetyl-3-hydroxy-2-(3,3,3-trifluoropropyl)-phenoxy]-propoxy}-aniline.

The starting material can be prepared, for example, as follows.

A spatula-tip of potassium iodide and 9.5 g of 4-(3-bromopropoxy)-2-hydroxy-3-(3,3,3-trifluoropropyl)-acetophenone are added to a suspension of 5.1 g of 4-methyl-3-nitrophenol and 4.6 g of calcined potassium carbonate in 100 ml of ethyl methyl ketone and the mixture is refluxed for 14 hours. The reaction mixture is cooled, poured onto water and extracted three times with ether. The organic phases are washed with water, combined, dried over sodium sulfate and concentrated to dryness under reduced pressure. Crystallisation of the residue gives 3-{3-[4-acetyl-3-hydroxy-2-(3,3,3-trifluoropropyl)-phenoxy]-propoxy}-6-methyl-nitrobenzene.

3-{3-[4-Acetyl-3-hydroxy-2-(3,3,3-trifluoropropyl)-phenoxy]-propoxy}-nitrobenzene is obtained in an analogous manner starting from m-nitrophenol.

1.0 g of Raney nickel is added to a solution of 9.1 g (23.5 mmol) of 3-[3-(4-acetyl-3-hydroxy-2-n-propylphenoxy)-propoxy]-6-methyl-nitrobenzene in 90 ml of tetrahydrofuran and the starting substance is hydrogenated at room temperature. The catalyst is filtered off and washed with tetrahydrofuran. The filtrate is evaporated to dryness under reduced pressure. 3-{3-[4-Acetyl-3-hydroxy-2-(3,3,3-trifluoropropyl)-phenoxy]-propoxy}-6-methyl-aniline is thus obtained.

3-{3-[4-Acetyl-3-hydroxy-2-(3,3,3-trifluoropropyl)-phenoxy]-propoxy}-aniline (ether/petroleum ether) is obtained. in an analogous manner starting from 3-{3-[4-acetyl-3-hydroxy-2-(3,3,3-trifluoropropyl)-phenoxy]-propoxy}-nitrobenzene.

EXAMPLE 6

20 ml of 1N sodium hydroxide solution are added to a suspension of 8.60 g (19.4 mmol) of methyl N-{{3-{3-[4-acetyl-3-hydroxy-2-(3,3,3-trifluoropropyl)-phenoxy]-propoxy}-6-methyl-phenyl}}-oxamate in 60 ml of methanol and 20 ml of water and the mixture is refluxed for 10 minutes. The reaction mixture is cooled and the product which has precipitated out is filtered off. The sodium salt of N-{{3-{3-[4-acetyl-3-hydroxy-2-(3,3,3-trifluoropropyl)-phenoxy]-propoxy}-6-methyl-phenyl}}-oxamic acid is thus obtained.

The sodium salt of N-{{3-{3-[4-acetyl-3-hydroxy-2-(3,3,3-trifluoropropyl)-phenoxy]-propoxy}-phenyl}}-oxamic acid can be prepared in an analogous manner.

EXAMPLE 7

The following compounds are obtained in a manner analogous to that described in Example 2: methyl N-{{3-{3-4-acetyl-3-hydroxy-2-(3,3,3-trifluoropropyl)-phenoxy]-propoxy}-2-methyl-pheny}}-oxamate; methyl N-{{3-{5-[4-acetyl-3-hydroxy-2-(3,3,3-trifluoropropyl)-phenoxy]-pentoxy}-phenyl}}-oxamate; methyl N-{{4-{3-[4-acetyl-3-hydroxy-2-(3,3,3-trifluoropropyl)-phenoxy]-propoxy}-3-methoxy-phenyl}}-oxamate; methyl N-{{4-{3-[4-acetyl-3-hydroxy-2-(3,3,3-trifluoropropyl)-phenoxy]-propoxy}-2-methyl-phenyl}}-oxamate; methyl N-{{2-{3-[4-acetyl-3-hydroxy-2-(3,3,3-trifluoropropyl)-phenoxy]-propoxy}-phenyl}}-oxamate; methyl N-{{4-{3-[4-acetyl-3-hydroxy-2-(3,3,3-trifluoropropyl)-phenoxy]-propoxy}-phenyl}}-oxamate; methyl N-{{3-{3-[4-acetyl-3-hydroxy-2-(3,3,3-trifluoropropyl)-phenoxy]-propoxy}-4-chloro-6-trifluoromethyl-phenyl}}-oxamate; methyl N-{{3-{3-[4-acetyl-3-hydroxy-2-(3,3,3-trifluoropropyl)-phenoxy]-propoxy}-2,4,6-trichloro-phenyl}}-oxamate as an oil and methyl N-{{3-{3-[4-acetyl-3-hydroxy-2-(3,3,3-trifluoropropyl)-phenoxy]-propoxy}-4,6-dimethyl-phenyl}}-oxamate.

The starting materials can be prepared, for example, in a manner analogous to that described in Example 1:

EXAMPLE 8

N-{{3-{3-[4-Acetyl-3-hydroxy-2-(3,3,3-trifluoropropyl)-phenoxy]-propoxy}-2-methyl-phenyl}}-oxamic acid and the triethanolammonium salt thereof; N-{{3-{5-[4-acetyl-3-hydroxy-2-(3,3,3-trifluoropropyl)-phenoxy]-pentoxy}-phenyl}}-oxamic acid and the triethanolammonium salt thereof; N-{{3-{3-[4-acetyl-3-hydroxy-2-(3,3,3-trifluoropropyl)-phenoxy]-propoxy}-4-chloro-6-trifluoromethyl-phenyl}}-oxamic acid and the triethanolammonium salt thereof; N-{{3-{3-[4-acetyl-3-hydroxy-2-(3,3,3-trifluoropropyl)-phenoxy]-propoxy}-2,4,6-trichloro-phenyl}}-oxamic acid and the triethanolammonium salt thereof and N-{{3-{3-[4-acetyl-3-hydroxy-3-(3,3,3-trifluoropropyl)-phenoxy]-propoxy}-4,6-dimethyl-phenyl}}-oxamic acid and the triethanolammonium salt thereof are obtained in a manner analogous to that described in Example 3.

EXAMPLE 9

18 ml of N sodium hydroxide solution are added to a solution of 7.95 g of methyl N-{{4-{3-[4-acetyl-3-hydroxy-2-(3,3,3-trifluoropropyl)-phenoxy]-propoxy}-3-methoxy-phenyl}}-oxamate in 100 ml of methanol and the mixture is refluxed for 1 hour. The hot solution is then poured into 200 ml of 0.1N hydrochloric acid. The product which has precipitated out is filtered off, washed with water and dried over phosphorus pentoxide in a drying cabinet. The N-{{4-{3-[4-acetyl-3-hydroxy-2-(3,3,3-trifluoropropyl)-phenoxy]-propoxy}-3-methoxy-phenyl}}-oxamic acid thus obtained is dissolved hot again in 100 ml of methanol, and one equivalent of triethanolamine in 10 ml of methanol, and one addition of 400 ml of ether, crystallisation starts. The equivalent triethanolammonium salt of N-{{4-{3-[4-acetyl-3-hydroxy-2-(3,3,3-trifluoropropyl)-phenoxy]-propoxy}-3-methoxy-phenyl}}-oxamic acid is thus obtained.

The following compounds are obtained in an analogous manner: N-{{4-{3- [4-acetyl-3-hydroxy-2-(3,3,3-trifluoropropyl)-phenoxy]-propoxy}-2-methyl-phenyl}}-oxamic acid and the triethanolammonium salt thereof; N-{{2-{3-[4-acetyl-3-hydroxy-2-(3,3,3-trifluoropropyl)-phenoxy]-propoxy}-phenyl}}-oxamic acid and the triethanolammonium salt thereof; and N-{{4-{3-[4-acetyl-3-hydroxy-2-(3,3,3-trifluoropropyl)-phenoxy]-propoxy}-phenyl}}-oxamic acid and the triethanolammonium salt thereof.

EXAMPLE 10

N-{{3-{3-[4-acetyl-3-hydroxy-2-(3,3,3-trifluoropropyl)-phenoxy]-propoxy}-phenyl}}-1H-tetrazole-5-carboxamide (melting point 110°-120° C. [decomposition]) is obtained in a manner analogous to that described in Example 1 by refluxing N-{{3-{3-[4-acetyl-3-hydroxy-2-(3,3,3-trifluoropropyl)-phenoxy]-propoxy}-phenyl}}-1-(4-methoxybenzyl)-tetrazole-5-carboxamide in trifluoroacetic acid/anisole.

The triethanolammonium salt of N-{{3-{3-[4-acetyl-3-hydroxy-2-(3,3,3-trifluoropropyl)-phenoxy]-propoxy}-phenyl}}-1H-tetrazole-5-carboxamide is obtained in a manner analogous to that described in Example 4 by dissolving the free compound in hot acetone and reacting it with triethanolamine.

EXAMPLE 11

A solution of 12.3 ml of ethyl chlorooxalate in 30 ml of methylene chloride is added dropwise to a solution, cooled to 0° C., of 43.6 g of 3-{3-[plus 4-acetyl-3-hydroxy-(3,3,3-trifluoropropyl)-phenoxy]-propoxy}-4-bromo-6-methylaniline and 15.3 ml of triethylamine in 400 ml of methylene chloride in the course of about 5 minutes and the mixture is then stirred at room temperature for a further 90 minutes. The reaction mixture is poured onto ice-water and the organic phase is separated off, washed with water, dried over sodium sulfate and concentrated under reduced pressure. Crystallisation from ethyl acetate/ether/petroleum ether gives ethyl N-{{3-{3-[4-acetyl-3-hydroxy-2-(3,3,3-trifluoropropyl)-phenoxy]-propoxy}-4-bromo-6-methyl-phenyl}}-oxamate.

EXAMPLE 12

448 mg (7.5 mmol) of potassium hydroxide are added to a suspension of 4.0 g of ethyl N-{{3-{3-[4-acetyl-3-hydroxy-2-(3,3,3-trifluoropropyl)-phenoxy]-propoxy}-4-bromo-6-methyl-phenyl}}-oxamate in 400 ml of ethanol and the mixture is refluxed for 4 hours. The reaction mixture is cooled and the product which has precipitated out is filtered off. The potassium salt of N-{{3-{3-[4-acetyl-3-hydroxy-2-(3,3,3-trifluoropropyl)-phenoxy]-propoxy}-4-bromo-6-methyl-phenyl}}-oxamic acid is thus obtained.

The sodium salt of N-{{3-{3-[4-acetyl-3-hydroxy-2-(3,3,3-trifluoropropyl)-phenoxy]-propoxy}-4-bromo-6-methyl-phenyl}}-oxamic acid can also be prepared in an analogous manner.

EXAMPLE 13

4.06 g of N-{{3-{3-[4-acetyl-3-hydroxy-2-(3,3,3-trifluoropropyl)-phenoxy]-propoxy}-4-bromo-6-methyl-phenyl}}-oxamic acid are dissolved in 40 ml of acetone, and a solution of 840 mg of diethanolamine in 5 ml of acetone is added. After addition of ether, crystallisation starts. The product which has precipitated out is filtered off and washed with ether. The diethanolammonium salt of N-{{3-{3-[4-acetyl-3-hydroxy-2-(3,3,3-trifluoropropyl)-phenoxy]-propoxy}-4-bromo-6-methyl-phenyl}}-oxamic acid is thus obtained.

The tris(hydroxymethyl)-methylammonium salt of N-{{3-{3-[4-acetyl-3-hydroxy-2-n-(3,3,3-trifluoropropyl)-phenoxy]-propoxy}-4-bromo-6-methyl-phenyl}}-oxamic acid can also be prepared in an analogous manner.

EXAMPLE 14

A solution of 7.05 g of N-{{3-{3-[4-acetyl-3-hydroxy-2-(3,3,3-trifluoropropyl)-phenoxy]-propoxy}-2-cyano-phenyl}}-1-(4-methoxybenzyl)-tetrazole-5-carboxamide in 150 ml of trifluoroacetic acid and 15 ml of anisole is refluxed for 30 minutes. The reaction mixture is concentrated under reduced pressure, about 200 ml of ether and 300 ml of petroleum ether are added and the crystals are filtered off. The N-{{3-{3-[4-acetyl-3-hydroxy-2-(3,3,3-trifluoropropyl)-phenoxy]-propoxy}-2-cyano-phenyl}}-1H-tetrazole-5-carboxamide thus obtained of melting point 206°-208°, is dissolved hot in 50 ml of acetone, and the calculated amount of triethanolamine in 30 ml of acetone is added. After addition of ether, crystallisation starts. The triethanolammonium salt of N-{{3-{3-[4-acetyl-3-hydroxy-2-(3,3,3-trifluoropropyl)phenoxy]-propoxy}-2-cyano-phenyl}}-1H-tetrazole-5-carboxamide is thus obtained.

The following compounds can be prepared in an analogous manner by refluxing N-{{3-{3-[4-acetyl-3-hydroxy-2-(3,3,3-trifluoropropyl)-phenoxy]-propoxy}-4-cyano-6-methylphenyl}}-1-(4-methoxybenzyl)-tetrazole-5-carboxamide and N-{{3-{3-[4-acetyl-3-hydroxy-2-(3,3,3-trifluoropropyl)-phenoxyl]-propoxy}-4-fluoro-6-methyl-phenyl}}-1-(4-methoxybenzyl)-tetrazole-5-carboxamide, respectively, in trifluoroacetic acid/anisole:

N-{{3-{3-[4-acetyl-3-hydroxy-2-(3,3,3-trifluoropropyl)-phenoxy]-propoxy}-4-cyano-6-methyl-phenyl}}-1H-tetrazole-5-carboxamide (melting point 245°-246° C.) and N-{{3-{3-[4-acetyl-3-hydroxy-2-(3,3,3-trifluoropropyl)-phenoxy]-propoxy}-4-fluoro-6-methyl-phenyl}}-1H-tetrazole-5-carboxamide.

The starting material can be prepared, for example, as follows:

A spatula-tip of potassium iodide and 31.5 g of 4-(3-bromopropoxy)-2-hydroxy-3-(3,3,3-trifluoropropyl)-acetophenone are added to a suspension of 13.1 g of 2-cyano-3-nitrophenol and 13.8 g of calcined potassium carbonate in 100 ml of ethyl methyl ketone and the mixture is refluxed for 20 hours. The reaction mixture is cooled, poured onto water and extracted three times with methylene chloride. The organic phases are washed with water, combined, dried over sodium sulfate and concentrated to dryness under reduced pressure. Crystallisation of the residue from ether/hexane gives 2-{3-[4-acetyl-3-hydroxy-2-(3,3,3-trifluoropropyl)-phenoxy]-propoxy}-6-nitro-benzonitrile.

2.5 g of 10% Pd-on-charcoal are added to a solution of 10 g of 2-{3-[4-acetyl-3-hydroxy-2-(3,3,3-trifluoropropyl)phenoxy]-propoxy}-6-nitro-benzonitrile and 10 g of cyclohexene in 500 ml of ethanol and the mixture is refluxed for 30 minutes. After cooling to room temperature, it is filtered and freed from the solvent. Ether is added to the residue and the crystals which have separated out are filtered off. 2-Amino-6-{3-[4-acetyl-3-hydroxy-2-(3,3,3-trifluoropropyl)-phenoxyl]-propoxy}-benzonitrile is obtained.

1.84 ml (21.5 mmol) of oxalyl chloride are added to a suspension of 5.8 g of potassium 1-(4-methoxybenzyl)-tetrazole-5-carboxylate in 110 ml of benzene and 1.0 ml of pyridine at 0°-5° and the mixture is stirred at room temperature for 30 minutes. The reaction mixture is concentrated under reduced pressure, the residue is taken up in benzene and the mixture is evaporated again under reduced pressure. The residue is dissolved in 80 ml of methylene chloride and the solution is added dropwise to a solution of 6.3 g of 2-amino-6-{3-[4-acetyl-3-hydroxy-2-(3,3,3-trifluoropropyl)-phenoxy]-propoxy}-benzonitrile and 1.72 ml of pyridine in 40 ml of methylene chloride at 0°-5° in the course of about 10 minutes. The mixture is then stirred at room temperature for 3 hours. The reaction mixture is diluted with methylene chloride and washed three times with water. The organic phases are combined, dried over sodium sulfate and evaporated under reduced pressure. Crystallisation of the residue from ethyl acetate/hexane gives N-{{3-{3-[4-acetyl-3-hydroxy-2-(3,3,3-trifluoropropyl)-phenoxy]-propoxy}-2-cyano-phenyl}}-1-(4-methoxybenzyl)-tetrazole-5-carboxamide.

EXAMPLE 15

The following compounds are furthermore obtained in a manner analogous to that described in Examples 1-14: methyl N-{{3-{3-[4-acetyl-3-hydroxy-2-(3,3,3-trifluoropropyl)-phenoxy]-propoxy}-4-methyl-6-chloro-phenyl}}-oxamate; methyl N-{{3-{3-[4-acetyl-3-hydroxy-2-(3,3,3-trifluoropropyl)-phenoxy]-propoxy}-4-methyl-6-bromo-phenyl}}-oxamate; N-{{3-{3-[4-acetyl-3-hydroxy-2-(3,3,3-trifluoropropyl)-phenoxy]-propoxy}-4-methyl-6-chloro-phenyl}}-oxamic acid and the triethanolammonium salt thereof; N-{{3-{3-[4-acetyl-3-hydroxy-2-(3,3,3-trifluoropropyl)-phenoxy]-propoxy}-4-methyl-6-chloro-phenyl}}-1H-tetrazole-5-carboxamide and the triethanolammonium salt thereof; N-{{3-{3-[4-acetyl-3-hydroxy-2-(3,3,3-trifluoropropyl)-phenoxy]-propoxy}-4-methyl-6-bromo-phenyl}}-1H-tetrazole-5-carboxamide and the triethanolammonium salt thereof; and ethyl N-{{3-{3-[4-acetyl-3-hydroxy-2-(3,3,3-trifluoropropyl)-phenoxy]-propoxy}-2-cyano-phenyl}}-oxamate.

EXAMPLE 16

3.0 g of boron tribromide are added dropwise to a solution, cooled to −78° C., of 2.2 g of methyl N-{{3-{3-[4-acetyl-3-methoxy-2-(3,3,3-trifluoropropyl)-phenoxy]-propoxy}-phenyl}}-oxamate in 20 ml of methylene chloride in the course of 5 minutes. The mixture is then stirred at room temperature for 6 hours. 5 ml of water are added, with cooling, and the organic phase is separated off and evaporated under reduced pressure. Recrystallisation from methylene chloride/ether gives methyl N-{{3-{3-[4-acetyl-3-hydroxy-2-(3,3,3-trifluoropropyl)-phenoxy]-propoxy}-phenyl}}-oxamate.

The starting material can be prepared, for example, as follows:

5,530 mg of sodium hydride are added to a solution of 7.46 g of 3-{3-[4-acetyl-3-hydroxy-2-(3,3,3-trifluoropropyl)-phenoxy]-propoxy}-nitrobenzene in 75 ml of dimethylformamide and the reaction mixture is warmed to 40°. 5.7 g of methyl iodide are added dropwise in the course of 15 minutes. Thereafter, the reaction mixture is kept at 40° C. for a further hour. After cooling, it is poured onto dilute hydrochloric acid and extracted with methylene chloride and the extract is evaporated. Recrystallisation from ether/hexane gives 3-{3-[4-acetyl-3-methoxy-2-(3,3,3-trifluoropropyl)-phenoxy]-propoxy}-nitrobenzene.

2.0 g of Raney nickel are added to a solution of 10 g of 3-{3-[4-acetyl-3-methoxy-2-(3,3,3-trifluoropropyl)-phenoxy]-propoxy}-nitrobenzene in 100 ml of tetrahydrofuran and the starting substance is hydrogenated at room temperature. The catalyst is filtered off and washed with tetrahydrofuran. Evaporation of the filtrate under reduced pressure gives 3-{3-[4-acetyl-3-methoxy-2-(3,3,3-trifluoropropyl)-phenoxy]-propoxy}-aniline as a colourless oil.

A solution of 3.45 ml of methyl chlorooxalate in 10 ml of methylene chloride is added dropwise to a solution of 9.2 g of 3-{3[4-acetyl-3-methoxy-2-(3,3,3-trifluoropropyl)-phenoxy]-propoxy}-aniline and 4.3 ml of triethanolpropy amine in 90 ml of methylene chloride in the course of 10 minutes. After stirring at room temperature for 5 hours, the mixture is poured onto water and extracted with methylene chloride. Evaporation of the extracts and recrystallisation of the residue from ether gives methyl N-{{3-{3-[4-acetyl-3-methoxy-2-(3,3,3-trifluoropropyl)-phenoxy]-propoxy}-phenyl}}-oxamate.

EXAMPLE 17

A spatula-tip of potassium iodide and 3.2 g of methyl N-[3-(3-bromopropoxy)-phenyl]-oxamate are added to a suspension of 2.3 g of 2,4-dihydroxy-3-(3,3,3-trifluoropropyl)-acetophenone and 1.6 g of calcined potassium carbonate in 40 ml of ethyl methyl ketone and the mixture is refluxed for 8 hours. The reaction mixture is cooled, poured onto water and extracted three times with methylene chloride. The combined extracts are washed with water, dried over sodium sulfate and concentrated to dryness under reduced pressure. Crystallisation of the residue from ether gives methyl N-{{3-{3-[4-acetyl-3-hydroxy-2-(3,3,3-trifluoropropyl)-phenoxy)-propoxy}-phenyl}}-oxamate.

The starting material can be prepared, for example, as follows:

43 ml of 1,3-dibromopropane are added to a suspension of 29 g of potassium carbonate and 0.5 g of potassium iodide in 170 ml of acetone and the mixture is refluxed. A solution of 19.4 g of 3-nitrophenol is then added dropwise in the course of 2 hours and the mixture is refluxed for a further 15 hours. The reaction mixture is filtered hot and evaporated. Chromatography of the residue on silica gel with toluene gives 3-(3-bromopropoxy)-nitrobenzene as a pale yellow oil.

1 g of Raney nickel is added to a solution of 4 g of 3-(3-bromopropoxy)-nitrobenzene in 40 ml of tetrahydrofuran and the starting substance is hydrogenated at room temperature. The catalyst is filtered off and washed with tetrahydrofuran. Evaporation of the filtrate gives 3-(3-bromopropoxy)-aniline as a colourless oil.

A solution of 1.5 ml of oxalic acid monomethyl ester chloride in 10 ml of methylene chloride is added dropwise to a solution of 3.5 g of 3-(3-bromopropoxy)-aniline and 1.3 ml of pyridine in 40 ml of methylene chloride in the course of 10 minutes. After stirring at room temperature for 2 hours, the mixture is poured onto water and extracted with methylene chloride. The combined extracts are evaporated and the residue is chromatographed on silica gel with methylene chloride/ethyl acetate (10:1). The eluate is evaporated and the residue is crystallised from ether/hexane. Methyl N-[3-(3-bromopropoxy)-phenyl]-oxamate of melting point 90°-91° is obtained.

EXAMPLE 18

A spatula-tip of potassium iodide and 3.15 g of 4-(3-bromopropoxy)-2-hydroxy-3-(3,3,3-trifluoropropyl)-acetophenone are added to a suspension of 1.8 g of methyl N-(3-hydroxyphenyl)-oxamate and 1.38 g of calcined potassium carbonate in 20 ml of ethyl methyl ketone and the mixture is refluxed for 12 hours. The reaction mixture is cooled, poured onto water and extracted three times with methylene chloride. The combined extracts are washed with water, dried over sodium sulfate and concentrated to dryness under reduced pressure. Crystallisation of the residue from methylene chloride/ether gives methyl N-{{3-{3-[4-acetyl-3-hydroxy-2-(3,3,3-trifluoropropyl)-phenoxy]-propoxy}-phenyl}}-oxamate.

The starting material is obtained, for example as follows:

A solution of 1.9 ml of methyl chlorooxalate in 10 ml of methylene chloride is added dropwise to a solution of 2.5 g of 3-aminoanisole and 1.5 ml of pyridine in 40 ml of methylene chloride in the course of 10 minutes. After stirring at room temperature for 3 hours, the mixture is poured onto water and extracted with methylene chloride. The extracts are dried over sodium sulfate and evaporated and the residue is crystallised from ether/hexane. Methyl N-(3-methoxyphenyl)-oxamate is obtained.

5 g of boron tribromide are added dropwise to a solution, cooled to −78° C., of 2 g of methyl N-(3-methoxyphenyl)-oxamate in 20 ml of methylene chloride in the course of 5 minutes. The mixture is stirred at room temperature for 5 hours, 5 ml of water are added, with cooling, and the organic phase is separated off. Drying over sodium sulfate and evaporation gives methyl N-(3-hydroxyphenyl)-oxamate.

EXAMPLE 19

The following compounds are furthermore obtained in a manner analogous to that described in Examples 1 to 14 and 16 to 18: N-{{3-{3-[4-acetyl-3-hydroxy-2-(3,3,3-trifluoropropyl)-phenoxy]-propoxy}-4-methox-

EXAMPLE 20

A suspension of 10.0 g of methyl N-{{3-{3-[4-acetyl-3-hydroxy-2-(3,3,3-trifluoropropyl)-phenoxy]-2-acetoxy-propoxy}-6-methyl-phenyl}}-oxamate in 60 ml of methanol and 100 ml of N sodium hydroxide solution is refluxed for 1 hour. The reaction mixture is cooled and acidified with dilute hydrochloric acid and the N-{{3-{3-[4-acetyl-3-hydroxy-2-(3,3,3-trifluoropropyl)-phenoxy]-2-hydroxy-propoxy}-6-methyl-phenyl}}-oxamic acid which has precipitated out is filtered off and washed with water. For purification, the product is dissolved in 200 ml of boiling methanol, 22 ml of N sodium hydroxide solution are added and the mixture is concentrated to about 100 ml under reduced pressure. After addition of acetone and ether, crystallisation starts. The product is filtered off and washed with ether. The sodium salt of N-{{3-{3-[4-acetyl-3-hydroxy-2-(3,3,3-trifluoropropyl)-phenoxy]-2-hydroxy-propoxy}-6-methyl-phenyl}}-oxamic acid is thus obtained.

N-{{4-{3-[4-Acetyl-3-hydroxy-2-(3,3,3-trifluoropropyl)-phenoxy]-2-hydroxy-propoxy}-3-methoxy-phenyl}}-oxamic acid can be prepared in an analogous manner starting from methyl N-{{4-{3-[4-acetyl-3-hydroxy-2-(3,3,3-trifluoropropyl)-phenoxy]-2-acetoxy-propoxy}-3-methoxy-phenyl}}-oxamate.

The starting materials are obtained, for example, as follows:

440 mg of a 55% sodium hydride suspension in mineral oil are added to a solution of 18.4 g of 4-methyl-3-nitrophenol in 180 ml of ethanol. A solution of 25.0 g of 4-(2,3-epoxypropoxy)-2-hydroxy-3-(3,3,3-trifluoropropyl)-acetophenone, obtainable by reaction of 2,4-dihydroxy-3-(3,3,3-trifluoropropyl)-acetophenone and epichlorohydrin, in 150 ml of ethanol is then added dropwise under reflux in the course of 1 hour and the mixture is subsequently stirred under reflux for 6 hours. The reaction mixture is cooled and concentrated to about 150 ml under reduced pressure and the concentrate is poured onto ice. The aqueous phase is acidified with dilute hydrochloric acid and extracted three times with methylene chloride. The organic phases are washed with water, combined, dried over sodium sulfate and concentrated under reduced pressure. Crystallisation of the residue from ether gives 3-{3-[4-acetyl-3-hydroxy-2-(3,3,3-trifluoropropyl-phenoxy]-2-hydroxy-propoxy}-6-methyl-nitrobenzene.

4-{3-[4-Acetyl-3-hydroxy-2-(3,3,3-trifluoropropyl)-phenoxy]-2-hydroxy-propoxy}-3-methoxy-nitrobenzene is obtained in an analogous manner starting from 4-hydroxy-3-methoxy-nitrobenzene and 4-(2,3-epoxypropoxy)-2-hydroxy-3-(3,3,3-trifluoropropyl)-acetophenone.

A suspension of 10.0 g of 3-{3-[4-acetyl-3-hydroxy-2-(3,3,3-trifluoropropyl)-phenoxy]-2-hydroxy-propoxy}-6-methylnitrobenzene in 100 ml of acetic anhydride and 1 ml of pyridine is stirred at 60° for 1 hour. The reaction mixture is then evaporated to dryness under reduced pressure and the crude 3-{3-[4-acetyl-3-hydroxy-2-(3,3,3-trifluoropropyl-phenoxy]-2-acetoxy-propoxy}-b 6-methyl-nitrobenzene thus obtained is acetoxy-propoxy}-6-methyl-nitrobenzene thus obtained is hydrogenated with Raney nickel in tetrahydrofuran. 3-{3-[4-Acetyl-3-hydroxy-2-(3,3,3-trifluoropropyl)-phenoxy]-2-acetoxy-propoxy}-6-methyl-aniline is obtained.

4-{3-[4-Acetyl-3-hydroxy-2-(3,3,3-trifluoropropyl)-phenoxy]-2-acetoxy-propoxy}-3-methoxy-aniline is obtained as an oil of Rf value=0.10 (silica gel; toluene/ethyl acetate=6:1) in an analogous manner starting from 4-{3-[4-acetyl-3-hydroxy-2-(3,3,3-trifluoropropyl)-phenoxy]-2-hydroxy-propoxy}-3-methoxy-nitrobenzene.

A solution of 1.9 ml of methyl chlorooxalate in 8 ml of methylene chloride is added dropwise to a solution, cooled to 0°, of 8.3 g of 3-{3-[4-acetyl-3-hydroxy-2-(3,3,3-trifluoropropyl)-phenoxy]-2-acetoxy-propoxy-}-6-methyl-aniline and 2.9 ml of triethylamine in 70 ml of methylene chloride in the course of about 5 minutes and the mixture is then stirred at room temperature for a further 2 hours. The reaction mixture is poured onto ice-water and the organic phase is separated off. The methylene chloride phase is washed with water, dried over sodium sulfate and evaporated under reduced pressure. Methyl N-{{3-{3-[4-acetyl-3-hydroxy-2-(3,3,3-trifluoropropyl)-phenoxy]-2-acetoxy-propoxy}-6-methyl-phenyl}}-oxamate is thus obtained as an oil with an Rf value=0.13 (silica gel; toluene/ethyl acetate=6:1).

Methyl N-{4-{3-[4-acetyl-3-hydroxy-2-(3,3,3-trifluoropropyl)-phenoxy]-2-acetoxy-propoxy}-3-methoxy-phenyl}-oxamate is obtained in an analogous manner starting from 4-{3-[4-acetyl-3-hydroxy-2-(3,3,3-trifluoropropyl)-phenoxy]-2-acetoxy-propoxy}-3-methoxy-aniline.

EXAMPLE 21

1.45 ml of ethyl chlorooxalate are added dropwise to a solution, cooled to 0°, of 5.5 g of 3-{3-[4-acetyl-3-hydroxy-2-(3,3,3-trifluoropropyl)-phenoxy]-2-hydroxy-propoxy}-4-bromo-6-methyl-aniline in 60 ml of methylene chloride, with rapid stirring. The reaction mixture is subsequently stirred at 0° for 40 minutes and at room temperature for 5 hours and poured onto ice-water and the organic phase is separated off. The methylene chloride phase is washed three times with 10 ml of water each time, dried over sodium sulfate and evaporated under reduced pressure. The residue is crystallised from ether/petroleum ether. Ethyl N-{{3-{3-[4-acetyl-3-hydroxy-2-(3,3,3-trifluoropropyl)-phenoxy]-2-hydroxy-propoxy}-4-bromo-6-methyl-phenyl}}-oxamate has a melting point of 113°-115°.

The starting material can be prepared as follows:

A mixture of 10.0 g of 2,4-dihydroxy-3-(3,3,3-trifluoropropyl)-acetophenone and 16.4 g of epibromohydrin in 20 ml of ethanol is refluxed and a solution of 2.46 g of potassium hydroxide in 20 ml of ethanol and 0.5 ml of water is added dropwise. The suspension is refluxed for 2 hours, cooled, diluted with 150 ml of water and extracted with 200 ml of methylene chloride. The methylene chloride phase is washed with 40 ml of water, dried over sodium sulfate and concentrated to dryness under reduced pressure. 4-(2,3-Epoxypropoxy)-2-hydroxy-3-(3,3,3-trifluoropropyl)-acetophenone is obtained as a yellow oil.

0.1 g of a dispersion of sodium hydride in mineral oil (55%) is added to a solution of 3.8 g of 2-bromo-4-methyl-5-nitro-phenol in 50 ml of anhydrous ethanol. The red solution is refluxed and a solution of 5.0 g of 4-(2,3-epoxypropoxy)-2-hydroxy-3-(3,3,3-trifluoropropyl)-acetophenone in 50 ml of anhydrous ethanol is added dropwise in the course of two hours, while passing in argon. The mixture is refluxed for 7 hours and cooled, 200 ml of water and 200 ml of methylene chloride are added and the mixture is acidified with 2N hydrochloric acid. The methylene chloride phase is separated off and the aqueous suspension is extracted again with 100 ml of methylene chloride. The combined methylene chloride phases are washed with 50 ml of water, dried over sodium sulfate and evaporated to dryness under reduced pressure. Crystallisation of the residue from ether/petroleum ether gives 3-{3-[4-acetyl-3-hydroxy-2-(3,3,3-trifluoropropyl)-phenoxy]-2-hydroxy-propoxy}-4-bromo-6-methyl-nitrobenzene as pale yellow crystals of melting point 127°-129°.

1.0 g of Raney nickel is added to a solution of 6.5 g of 3-{3-[4-acetyl-3-hydroxy-2-(3,3,3-trifluoropropyl)-phenoxy]-2-hydroxy-propoxy}-4-bromo-6-methyl-nitrobenzene in 65 ml of tetrahydrofuran and the starting substance is hydrogenated at room temperature. The catalyst is filtered off and washed with tetrahydrofuran. The filtrate is evaporated to dryness under reduced pressure and the residue is crystallised from ether/petroleum ether. 3-{3-[4-Acetyl-3-hydroxy-2-(3,3,3-trifluoropropyl)-phenoxy]-2-hydroxy-propoxy}-4-bromo-6-methyl-aniline has a melting point of 118°-120°.

EXAMPLE 22

A mixture of 3.3 g of ethyl N-{{3-{3-[4-acetyl-3-hydroxy-2-(3,3,3-trifluoropropyl)-phenoxy]-2-hydroxy-propoxy}-4-bromo-6-methyl-phenyl}}-oxamate in 40 ml of ethanol and 12.5 ml of N sodium hydroxide solution is refluxed for 2 hours. The reaction mixture is concentrated under reduced pressure, 50 ml of water are added and the mixture is acidified with 2N hydrochloric acid. The suspension is extracted with 100 ml of ethyl acetate. The ethyl acetate solution is separated off, washed with 20 ml of water dried with sodium sulfate and concentrated under reduced pressure. The residue is crystallised from ethyl acetate/petroleum ether. N-{{3-{3-[4-Acetyl-3-hydroxy-2-(3,3,3-trifluoropropyl)-phenoxy]-2-hydroxy-propoxy}-4-bromo-6-methyl-phenyl}}-oxamic acid has a melting point of 195°-196°.

EXAMPLE 23

2.6 g of N-{{3-{3-[4-acetyl-3-hydroxy-2-(3,3,3-trifluoropropyl)-phenoxy]-2-hydroxy-propoxy}-4-bromo-6-methyl-phenyl}}-oxamic acid are dissolved in 250 ml of acetone, and a solution of 1 ml of diethylamine in 10 ml of acetone is added. The reaction solution is concentrated to 30 ml under reduced pressure and ether is added, whereupon the diethylammonium salt of N-{{3-{3-[4-acetyl-3-hydroxy-2-(3,3,3-trifluoropropyl)-phenoxy]-2-hydroxy-propoxy}-4-bromo-6-methyl-phenyl}}-oxamic acid crystallises out. Melting point 160°-162°.

EXAMPLE 24

A solution of 6.2 g of N-{{3-{3-[4-acetyl-3-hydroxy-2-(3,3,3-trifluoropropyl)-phenoxy]-2-hydroxy-propoxy}-4-bromo-6-methyl-phenyl}}-1-(4-methoxybenzyl)-tetrazole-5-carboxamide in 130 ml of trifluoroacetic acid and 14 ml of anisole is refluxed for 30 minutes. The reaction mixture is concentrated under reduced pressure, about 200 ml of ether and 300 ml of petroleum ether are added and the crystals are filtered off. N-{{3-{3-[4-Acetyl-3-hydroxy-2-(3,3,3-trifluoropropyl)-phenoxy]-2-hydroxy-propoxy}-4-bromo-6-methyl-phenyl}}-1H-tetrazole-5-carboxamide is obtained.

The starting material can be prepared, for example, as follows:

1.0 ml of oxalyl chloride is added to a suspension of 3.0 g of potassium 1-(4-methoxy-benzyl)-tetrazole-5-carboxylate in 40 ml of benzene and 0.7 ml of pyridine at 0°-5° and the mixture is stirred at room temperature for 30 minutes. The reaction mixture is concentrated under reduced pressure, the residue is taken up in benzene and the mixture is evaporated again under reduced pressure. The residue is suspended in 300 ml of methylene chloride and the suspension is added dropwise to a solution of 4.2 g of 3-{3-[4-acetyl-3-hydroxy-2-(3,3,3-trifluoropropyl)-phenoxy]-2-hydroxy-propoxy}-4-bromo-6-methyl-aniline and 0.92 ml of pyridine in 40 ml of methylene chloride at 0°-5° in the course of 10 minutes. The mixture is then stirred for 3 hours at room temperature. The reaction mixture is diluted with methylene chloride and washed twice with water. The organic phase is dried over sodium sulfate and evaporated under reduced pressure. N-{{3-{3-[4-Acetyl-3-hydroxy-2-(3,3,3-trifluoropropyl)-phenoxy]-2-hydroxy-propoxy}-4-bromo-6-methyl-phenyl}}-1-(4-methoxy-benzyl)-tetrazole-5-carboxamide is obtained in the form of a yellow oil.

In an analogous manner the N-{{3-{3-[4-acetyl-3-hydroxy-2-(3,3,3-trifluoropropyl)-phenoxy]-2-hydroxy-propoxy}-4-fluoro-6-methyl-phenyl}}-1H-tetrazole-5-carboxamide can be prepared.

EXAMPLE 25

The following compounds are obtained in a manner analogous to that described in Example 2 by reaction of 3-{3-[4-acetyl-3-hydroxy-2-(3,3,3-trifluoropropyl)-phenoxy]-propoxy}-4-chloro-6-methyl-aniline, 3-{3-[4-acetyl-3-hydroxy-2-(3,3,3-trifluoropropyl)-phenoxy]-propoxy}-4-fluoro-6-methyl-aniline or 2-{3-[4-acetyl-3-hydroxy-2-(3,3,3-trifluoropropyl)-phenoxy]-propoxy}-4-amino-5-methyl-benzonitrile with methyl chlorooxalate or ethyl chlorooxalate methyl N-{{3-{3-[4-acetyl-3-hydroxy-2-(3,3,3-trifluoropropyl)-phenoxy]-propoxy}-4-chloro-6-methyl-phenyl}}-oxamate, ethyl N-{{3-{3-[4-acetyl-3-hydroxy-2-(3,3,3-trifluoropropyl)-phenoxy]-propoxy}-4-chloro-6-methyl-phenyl}}-oxamate, methyl N-{{3-{3-[4-acetyl-3-hydroxy-2-(3,3,3-trifluoropropyl)-phenoxy]-propoxy}-4-fluoro-6-methyl-phenyl}}-oxamate, ethyl N-{{3-{3-[4-acetyl-3-hydroxy-2-(3,3,3-trifluoropropyl)-phenoxy]-propoxy}-4-fluoro-6-methyl-phenyl}}-oxamate, methyl N-{{3-{3-[4-acetyl-3-hydroxy-2-(3,3,3-trifluoropropyl)-phenoxy]-propoxy}-4-cyano-6-methyl-phenyl}}-oxamate and ethyl N-{{3-{3-[4-acetyl-3-hydroxy-2-(3,3,3-trifluoropropyl)-phenoxy]-propoxy}-4-cyano-6-methyl-phenyl}}-oxamate.

EXAMPLE 26

The following compounds are obtained in a manner analogous to that described in Example 3, 6 or 12 by hydrolysis of methyl or ethyl N-{{3-{3-[4-acetyl-3-hydroxy-2-(3,3,3-trifluoropropyl)-phenoxy]-propoxy}-4-chloro-6-methyl-phenyl}}-oxamate, methyl or ethyl N-{{3-{3-[4-acetyl-3-hydroxy-2-(3,3,3-trifluoropropyl)-phenoxy]-propoxy}-4-fluoro-6-methyl-phenyl}}-oxamate or methyl or ethyl N-{{3-{3-[4-acetyl-3-hydroxy-2-(3,3,3-trifluoropropyl)-phenoxy]-propoxy}-4-cyano-6-methyl-phenyl}}-oxamate: N-{{3-{3-[4-acetyl-3-hydroxy-2-(3,3,3-trifluoropropyl)-phenoxy]-propoxy}-4-chloro-6-methyl-phenyl}}-oxamic acid and the sodium and potassium salt thereof, N-{{3-{3-[4-acetyl-3- hydroxy-2-(3,3,3-trifluoropropyl)-phenoxy]-propoxy}-4-fluoro-6-methyl-phenyl}}-oxamic acid and the sodium and potassium salt thereof and N-{{3-{3-[4-acetyl-3-hydroxy-2-(3,3,3-trifluoropropyl)-phenoxy]-propoxy}-4-cyano-6-methyl-phenyl}}-oxamic acid and the sodium and potassium salt thereof.

EXAMPLE 27

In a manner analogous to that described in Examples 2 to 5, 9, 11, 16 to 18 and 20 to 22 the N-{{3-{3-[4-acetyl-3-hydroxy-2-(3,3,3-trifluoropropyl)-phenoxy-propoxy}-2-cyano-phenyl}}-oxamic acid (melting point 152°-155° C.) and the triethanolammonium salt thereof (melting point 220°-250° C. [decomposition]) can be obtained.

EXAMPLE 28

In a manner analogous to that described in Example 24, by refluxing N-{{3-{3-[4-acetyl-3-hydroxy-2-(3,3,3-trifluoropropyl)-phenoxy]-2-hydroxy-propoxy}-4-chloro-6-methyl-phenyl}}-1-(4-methoxybenzyl)-tetrazole-5-carboxamide and N-{{3-{3-[4-acetyl-3-hydroxy-2-(3,3,3-trifluoropropyl)-phenoxy}-2-hydroxy-propoxy}-4-cyano-6-methylphenyl}}-1-(4-methoxybenzyl)-tetrazole-5-carboxamide, respectively, in trifluoroacetic acid/anisole, can be obtained:

N-{{3-{3-[4-acetyl-3-hydroxy-2-(3,3,3-trifluoropropyl)-phenoxy]-2-hydroxy-propoxy}-4-chloro-6-methyl-phenyl}}-1H-tetrazole-5-carboxamide (melting point 231°-235° C.) and N-{{3-{3-[4-acetyl-3-hydroxy-2-(3,3,3-trifluoropropyl)-phenoxy]-2-hydroxy-propoxy}-4-cyano-6-methylphenyl}}-1H-tetrazole-5-carboxamide (melting point 220°-223° C.).

EXAMPLE 29

A solution of 2.84 g (4.5 mmol) of N-{{3-{3-[4-acetyl-3-hydroxy-2-(3,3,3-trifluoropropyl)-phenoxy]-propoxy}-6-methyl-phenyl}}-1-(4-methoxybenzyl)-tetrazole-5-carboxamide in 90 ml of trifluoroacetic acid and 9 ml of anisole is refluxed for 60 minutes. The reaction mixture is concentrated under reduced pressure, about 150 ml of ether and 300 ml of petroleum ether are added and the crystals are filtered off. The N-{{3-{3-[4-acetyl-3-hydroxy-2-(3,3,3-trifluoropropyl)-phenoxy]-propoxy}-6-methyl-phenyl}}-1H-tetrazole-5-carboxamide thus obtained, of melting point 236°-238° C. (decomposition), is dissolved in 50 ml of tetrahydrofuran, and one equivalent of sodium, dissolved in 5 ml of methanol, is added. After addition of ether, crystallizations starts. The sodium salt of N-{{3-{3-[4-acetyl-3-hydroxy-2-(3,3,3-trifluoropropyl)-phenoxy]-propoxy}-6-methyl-phenyl}}-1H-tetrazole-5-carboxamide of melting point 115°-125° C. (decomposition) is thus obtained.

The starting material can be prepared, for example, in a manner analogous to that described in Example 1.

EXAMPLE 30

In a manner analogous to that described in Example 20 the N-{{3-{3-[4-acetyl-3-hydroxy-2-(3,3,3-trifluoropropyl)-phenoxy]-2-hydroxy-propyloxy}-2-cyano-phenyl}}-oxamic acid can be obtained by refluxing a suspension of methyl N-{{3-{3-[4-acetyl-3-hydroxy-2-(3,3,3-trifluoropropyl)-phenoxy]-2-acetoxy-propyloxy}-2-cyano-phenyl}}-oxamate in methanol and N sodium hydroxide solution, cooling and acidifying of the reaction mixture with dilute hydrochloric acid. The N-{{3-{3-4-acetyl-3-hydroxy-2-(3,3,3-trifluoropropyl)-phenoxy]-2-hydroxy-propyloxy}-2-cyanophenyl}}-oxamic acid is recrytallized from acetone/diethyl ether and crystallizes with 0.5 equivalents of diethyl ether (melting point 83°-90° C.). The sodium salt of N-{{3-{3-[4-acetyl-3-hydroxy-2-(3,3,3-trifluoropropyl)-phenoxy]-2-hydroxy-propyloxy}-2-cyano-phenyl}}-oxamic acid is obtained in a manner analogous to that described in Example 20.

The starting material is obtained, for example, in a manner analogous to that described in Example 20.

EXAMPLE 31

Another of the oxamic acid or 5-tetrazolecarboxamide compounds mentioned in the above examples can be converted into its diethanolammonium, tris(hydroxymethyl)methylammonium or diethylammonium salt in a manner analogous to that described in Examples 13 and 23.

EXAMPLE 32

Tablets containing 25 mg of active ingredient, for example the triethanolammonium salt of N-{{3-{3-[4-acetyl-3-hydroxy-2-(3,3,3-trifluoropropyl)-phenoxy]-propoxy}-4-chloro-6-methyl-phenyl}}-oxamic acid, can be prepared as follows:

Constituents (for 1,000 tablets)

| | |
|---|---|
| Active ingredient | 25.0 g |
| Lactose | 100.7 g |
| Wheat starch | 7.5 g |
| Polyethylene glycol 6000 | 5.0 g |
| Talc | 5.0 g |
| Magnesium stearate | 1.8 g |
| demineralised water | q.s. |

Preparation

All the solid ingredients are first forced through a sieve of 0.6 mm mesh width. The active ingredient, the lactose, the talc, the magnesium stearate and half of the starch are then mixed. The other half of the starch is suspended in 40 ml of water, this suspension is added to a boiling solution of the polyethylene glycol in 100 ml of water and the mixture is granulated, if necessary with the addition of water. The granules are dried overnight at 35°, forced through a sieve of 1.2 mm mesh width and compressed to tablets, concave on both sides, of about 6 mm diameter.

Tablets containing in each case 25 mg of another of the compounds of the formula I mentioned in Examples 1 to 31 can also be prepared in an analogous manner, it being possible for compounds in which $R_8$ is carboxyl or 5-tetrazolyl to be in the form of salts with bases, for example as the sodium salt or triethanolammonium salt, or in the free form.

EXAMPLE 33

Tablets for chewing, containing 30 mg of active ingredient, for example the triethanolammonium salt of N-{{3-{3-[4-acetyl-3-hydroxy-2-(3,3,3-trifluoropropyl)-phenoxy]-propoxy}-4-chloro-6-methyl-phenyl}}-oxamic acid, can be prepared, for example, as follows:

Composition (for 1,000 tablets)

| | |
|---|---|
| Active ingredient | 30.0 g |
| Mannitol | 267.0 g |

| | |
|---|---|
| -continued | |
| Lactose | 179.5 g |
| Talc | 20.0 g |
| Glycine | 12.5 g |
| Stearic acid | 10.0 g |
| Saccharin | 1.0 g |
| 5% gelatine solution | q.s. |

Preparation

All the solid ingredients are first forced through a sieve of 0.25 mm mesh width. The mannitol and the lactose are mixed, the mixture is granulated, with the addition of gelatine solution, and the granules are forced through a sieve of 2 mm mesh width, dried at 50° and again forced through a sieve of 1.7 mm mesh width. The active ingredient, the glycine and the saccharin are mixed thoroughly, the mannitol, the lactose granules, the stearic acid and the talc are added and the entire mass is mixed thoroughly and compressed to tablets concave on both sides and of 10 mm diameter, with a breaking notch on the upper side.

Tablets containing in each case 30 mg of another of the compounds of the formula I mentioned in Examples 1 to 31 can also be prepared in an analogous manner, it being possible for compounds in which $R_8$ is carboxyl or 5-tetrazolyl to be in the free form or in the form of salts with bases, for example as the sodium salt or triethanolammonium salt.

EXAMPLE 34

Tablets containing 100 mg of active ingredient, for example the triethanolammonium salt of N-{3-{3-[4-acetyl-3-hydroxy-2-(3,3,3-trifluoropropyl)-phenoxy]-propoxy}-4-chloro-6-methyl-phenyl}-oxamic acid, can be prepared as follows:

Composition (for 1,000 tablets)

| | |
|---|---|
| Active ingredient | 100.0 g |
| Lactose | 248.5 g |
| Maize starch | 17.5 g |
| Polyethylene glycol 6000 | 5.0 g |
| Talc | 15.0 g |
| Magnesium stearate | 4.0 g |
| demineralised water | q.s. |

Preparation

The solid ingredients are first forced through a sieve of 0.6 mm mesh width. The active ingredient, lactose, talc, magnesium stearate and half of the starch are then intimately mixed. The other half of the starch is suspended in 65 ml of water and this suspension is added to a boiling solution of the polyethylene glycol in 260 ml of water. The resulting paste is added to the powdered substances and the entire mass is mixed and granulated, if necessary with the addition of water. The granules are dried overnight at 35° forced through a sieve of 1.2 mm mesh width and compressed to tablets concave on both sides and about 10 mm in diameter, with a breaking notch on the upper side.

Tablets containing 100 mg of another compound of the formula I according to Examples 1 to 31 can also be prepared in an analogous manner, it being possible for compounds in which $R_8$ is carboxyl or 5-tetrazolyl to be in the free form or in the form of salts with bases, for example as the sodium salt or triethanolammonium salt.

EXAMPLE 35

A propellant-containing inhalation suspension which forms a solid aerosol and contains 0.1% by weight of methyl N-{3-{3-[4-acetyl-3-hydroxy-2-(3,3,3-trifluoropropyl)-phenoxy]-propoxy}-4-chloro-6-methyl-phenyl}-oxamate (active ingredient) can be prepared, for example, as follows:

Composition

| | |
|---|---|
| Active ingredient, micronised | 0.1% by weight |
| "Sorbitan trioleate" | 0.5% by weight |
| Propellant A (trichlorotrifluoroethane) | 4.4% by weight |
| Propellant B (mixture of 15 parts of dichlorodifluoromethane and 80 parts of symmetric dichlorotetrafluoroethane) | q.s. |

Preparation

The active ingredient is suspended in the trichlorotrifluoroethane with exclusion of moisture, with the aid of a customary homogeniser and with the addition of the sorbitan trioleate, the suspension is introduced into a metered aerosol container and this is sealed and filled with the dichlorodifluoromethane/dichlorotetrafluoroethane mixture under pressure.

Inhalation suspensions containing another compound of the formula I according to Examples 1 to 31 can also be prepared in an analogous manner, it being possible for compounds in which $R_8$ is carboxyl or 5-tetrazolyl to be in the free form or in the form of salts with bases, for example as the sodium salt or triethanolammonium salt.

EXAMPLE 36

An approximately 2% aqueous solution of the triethanolammonium salt of N-{3-{3-[4-acetyl-3-hydroxy-2-(3,3,3-trifluoropropyl)-phenoxy]-propoxy}-4-chloro-6-methylphenyl}-oxamic acid as the active ingredient, which is suitable for inhalation, can be prepared, for example, in the following composition:

Composition

| | |
|---|---|
| Active ingredient | 2,000 mg |
| Stabiliser, for example disodium ethylenediaminetetraacetate | 10 mg |
| Preservative, for example benzalkonium chloride | 10 mg |
| Water, freshly distilled    to | 100 ml |

Preparation

The active ingredient is dissolved in freshly distilled water. The stabiliser and the preservative are then added. After complete solution of all the components, the resulting solution is made up to 100 ml and introduced into bottles and these are sealed gas-tight.

2% Innalation solutions containing another active ingredient of one of Examples 1 to 31 can also be prepared in an analogous manner.

EXAMPLE 37

Capsules which are suitable for insufflation and contain about 25 mg of methyl N-{3-{3-[4-acetyl-3-hydroxy-2-(3,3,3-trifluoropropyl)-phenoxy]-propoxy}-4-chloro-6-methyl-phenyl}-oxamate as the active ingredient can be prepared, for example, in the following composition:

Composition

| Active ingredient | 25 g |
|---|---|
| Lactose, finely ground | 25 g |

Preparation

The active ingredient and the lactose are intimately mixed. The resulting powder is then sieved and introduced into 1,000 gelatine capsules in portions of in each case 50 mg.

Insufflation capsules containing in each case another active ingredient according to one of Examples 1 to 31 can also be prepared in an analogous manner.

What is claimed is:

1. A 2-fluoroalkylated 4-acylresorcinol ether of the formula

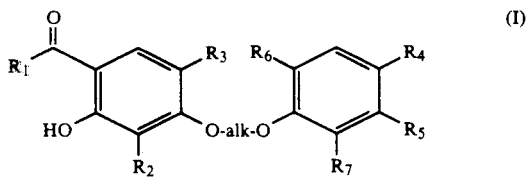

in which $R_1$ is lower alkyl having not more than 4 C atoms, $R_2$ is ω-fluoro-,ω, ω-difluoro- or ω,ω,ω-trifluoro-lower alkyl having not more than 4 C atoms, $R_3$ is hydrogen, $R_4$ is hydrogen, lower alkyl, trifluoromethyl or halogen with an atomic number of not more than 35, $R_5$ is 5-tetrazolyl carbonylamino, $R_6$ is hydrogen, lower alkyl having not more than 4 C atoms, halogen with an atomic number of not more than 35, trifluoromethyl, lower alkoxycarbonyl having not more than 5 C atoms, cyano or carbamyl, $R_7$ is hydrogen, lower alkyl having not more than 4 C atoms, halogen with an atomic number of not more than 35, carbamyl or cyano and alk is straight chain, terminally bonded lower alkylene having 2 to not more than 5 C atoms, or hydroxy-lower alkylene having 3 to not more than 7 C atoms, in which the hydroxyl group is bonded in a position higher than the α-position and lower than the ω-position, or a pharmaceutically acceptable salt thereof.

2. A compound as claimed in claim 1, in which $R_1$ is lower alkyl having not more than 4 C atoms, $R_2$ is ω, ω, ω-trifluoro-lower alkyl having not more than 3 C atoms, $R_3$ is hydrogen and $R_5$ is 5-tetrazolylcarbonylamino, $R_4$ is lower alkyl having not more than 4C atoms, $R_6$ is halogen with an atomic number of not more than 35, or cyano, $R_7$ is hydrogen, and alk is straight-chain, terminally bonded lower alkylene having 2 to not more than 5 C atoms, or hydroxy-lower alkylene having 3 to not more than 7 C atoms, in which the hydroxyl group is bonded in a position higher than the α-position and lower than the ω-position, or a pharmceutically acceptable salt thereof.

3. A compound as claimed in claim 1, in which $R_1$ is lower alkyl having not more than 4 C atoms, $R_2$ is ω-fluoro-, ω,ω-difluoro- or ω,ω,ω-trifluoro-lower alkyl having not more than 3 C atoms, $R_3$ and $R_7$ are hydrogen, $R_4$ is hydrogen or lower alkyl having not more than 4 C atoms, $R_6$ is hydrogen, cyano or halogen with an atomic number of not more than 35, $R_5$ is 5-tetrazolylcarbonylamino and alk is straight-chain, terminally bonded lower alkylene having 2 to not more than 5 C atoms, or hydroxy-lower alkylene having 3 to not more than 7 C atoms, in which the hydroxyl group is bonded in a position higher than the α-position and lower than the ω-position, or a pharmaceutically acceptable salt thereof.

4. A compound as claimed in claim 1 being N-{{3-{3-[4-Acetyl-3-hydroxy-2-(3,3,3-trifluoropropyl)-phenoxy]-propoxy}-4-chloro-6-methyl-phenyl}}-1H-tetrazole-5-carboxamide or a pharmaceutically acceptable salt thereof.

5. A compound as claimed in claim 1 being N-{{-3-{3-[4-Acetyl-3-hydroxy-2-(3,3,3-trifluoropropoyl)-phenoxy]-propoxy}-4-bromo-6-methyl-phenyl}}-1H-tetrazole-5-carboxamide or a pharmaceutically acceptable salt thereof.

6. A compound as claimed in claim 1 being N-{{3-{3-[4-acetyl-3-hydroxy-2-(3,3,3-trifluoropropyl)-phenoxy]-2-hydroxy-propoxy}-4-bromo 6-methyl-phenyl}}-1H-tetrazole-5-carboxamide or a pharmaceutically acceptable salt thereof.

7. A compound as claimed in claim 1 being N-{{3-{3-[4-acetyl-3-hydroxy-2-(3,3,3-trifluoropropyl)-phenoxy]-2-hydroxy-propoxy}-4-chloro-6-methyl-phenyl}}-1H-tetrazole-5-carboxamide or a pharmaceutically acceptable salt thereof.

8. A compound as claimed in claim 1 being N-{{3-{3-[4-acetyl-3-hydroxy-2-(3,3,3-trifluoropropyl)-phenoxy]-2-hydroxy-propoxy}-4-cyano-6-methyl-phenyl}}-1H-tetrazole-5-carboxamide or a pharmaceutically acceptable salt thereof.

9. A compound as claimed in claim 1 being N-{{3-{3-[4-acetyl-3-hydroxy-2-(3,3,3-trifluoropropyl)-phenoxy]-propoxy}-phenyl}}-1H-tetrazole-5-carboxamide or a pharmaceutically acceptable salt thereof.

10. A compound as claimed in claim 1 being N-{{3-{3-[4-acetyl-3-hydroxy-2-(3,3,3-trifluoropropyl)-phenoxy]-propoxy}-6-methyl-phenyl)}-1H-tetrazole-5-carboxamide or a pharmaceutically acceptable salt thereof.

11. A pharmaceutical composition containing a therapeutically effective amount of a compound according to claim 1 or a pharmaceutically acceptable salt thereof, in admixture to customary pharmaceutical adjuncts and/or carriers.

12. Method of treatment of allergies and/or inflammations characterised in that a therapeutically effective amount of a compound claimed in claim 1 or a pharmaceutically acceptable salt thereof is administered.

* * * * *